United States Patent [19]
Knipe et al.

[11] Patent Number: 5,869,234
[45] Date of Patent: Feb. 9, 1999

[54] METHOD OF IDENTIFYING COMPOUNDS WHICH MODULATE HERPESVIRUS INFECTION

[75] Inventors: David M. Knipe, Auburndale; Kai Xia, Allston, both of Mass.; Neal A. DeLuca, Cheswick, Pa.

[73] Assignee: President and Fellows of Harvard College, Cambridge, Mass.

[21] Appl. No.: 583,569

[22] Filed: Jan. 5, 1996

[51] Int. Cl.$^6$ .......................... C12Q 1/70; G01N 33/567
[52] U.S. Cl. .......................... 435/5; 435/7.21; 435/7.36; 435/7.72; 435/15
[58] Field of Search ................................ 435/15, 5, 7.21, 435/7.36, 7.72

[56] References Cited

U.S. PATENT DOCUMENTS

| | | |
|---|---|---|
| 5,047,237 | 9/1991 | Cochran . |
| 5,275,934 | 1/1994 | Post et al. . |
| 5,601,974 | 2/1997 | Post et al. . |

FOREIGN PATENT DOCUMENTS

| | | |
|---|---|---|
| WO 93/14785 | 8/1993 | WIPO . |
| WO 94/04920 | 3/1994 | WIPO . |
| WO 95/02071 | 1/1995 | WIPO . |

OTHER PUBLICATIONS

Xia, K., et al., "ICP4 Is a Substrate For Protein Kinases A and C", 17th International Herpesvirus Workshop, Heriot Watt University, Edinborough, Scotland, Aug. 1–7, 1992; abstract.

Faber, S.W. and Wilcox, K.W., "Characterization of a Herpes Simplex Virus Regulatory Protein: Aggregation and Phosphorylation of a Temperature–Sensitive Variant of ICP 4", *Archives of Virol.*, 91:297–312 (1986).

Samaniego, L.A., et al., "Functional Interactions Between Herpes Simplex Virus Immediate–Early Proteins During Infection: Gene Expression as a Consequence of ICP27 and Different Domains of ICP4", *J. of Virol.*, 69(9):5705–5715 (1995).

Paterson, T. and Everett, R.D., "A Prominent Serine–Rich Region in Vmw175, the Major Transcriptional Regulator Protein of Herpes Simplex Virus Type 1, is Not Essential for Virus Growth in Tissue Culture", *J. of Gen'l. Virol.*, 71:1775–1783 (1990).

Shepard, A.A., et al., "Separation of Primary Structural Components Conferring Autoregulation, Transactivation, and DNA–Binding Properties to the Herpes Simplex Virus Transcriptional Regulatory Protein ICP4", *J. of Virology*, 63(9):3714–3728 (1989).

Paterson T. and Everett, R.D., "Mutational Dissection of the HSV–1 Immediate–Early Protein Vmw175 Involved in Transcriptional Transactivation and Repression", *Virology*, 166:186–196 (1988).

DeLuca, N.A. and Schaffer, P.A., "Physical and Functional Domains of the Herpes Simplex Virus Transcriptional Regulatory protein ICP4", *J. Virology*, 62(3):732–743 (Mar. 1988).

DeLuca, N.A., et al., "Isolation and Characterization of Deletion Mutants of Herpes Simplex Virus Type 1 in the Gene Encoding Immediate–Early Regulatory Protein ICP4", *J. Virology*, 56(2 :558–570 (Nov. 1985).

Wilcox, K.W., et al., "Herpes Simplex Virus Phosphoproteins", *J. Virology*, 33(1):167–182 (Jan. 1980).

Papavassiliou, A.G., et al., "The Interaction of ICP4 With Cell/Infected–Cell Factors and Its State of Phosphorylation Modulate Differential Recognition of Leader Sequences in Herpes Simplex Virus DNA", *The EMBO J.*, 10(2):397–406 (1991).

Shepard, A.A. and DeLuca, N.A., "Activities of Heterodimers Composed of DNA–Binding– and transactivation–Deficient Subunits of the Herpes Simplex Virus Regulatory Protein ICP4", *J. of Virology*, 65(1):299–307 (Jan. 1991).

Preston, C.M., "Abnormal Properties of an Immediate Early Polypeptide in Cells Infected with the Herpes Simplex Virus Type 1 Mutant tsK", *J. of Virology*, 32(2):357–369 (Nov. 1979).

Pereira, L., et al., "Regulation of Herpesvirus Macromolecular Synthesis", *Virology*, 77:733–749 (1977).

Xia, K., et al., "Analysis of Phosphorylation Sites of Herpes Simplex Virus Type 1 ICP4", *Jour. of Virology* 70(2):1061–1071 (1996).

*Primary Examiner*—James O. Wilson
*Attorney, Agent, or Firm*—Hamilton, Brook, Smith & Reynolds, P.C.

[57] ABSTRACT

The present invention relates to a method of identifying a compound which modulates (enhances, inhibits, reduces) herpesvirus infection of a vertebrate cell comprising the steps of combining a phosphorylating enzyme capable of catalyzing the phosphorylation of ICP4, a substrate comprising a polypeptide which is phosphorylated by the enzyme, a phosphate source and the compound to be assessed; maintaining the combination under conditions appropriate for phosphorylation of the substrate; and determining phosphorylation of the substrate which occurs in the presence of the compound to be assessed. The present invention also relates to the compounds identified by the methods of the present invention.

26 Claims, 4 Drawing Sheets

142
A-P-L-R-G-A-Y-P-D-P-T-D-R-L-S-P

```
                            166                173
                             . . . . . . . .
R-P-P-A-Q-P-P-R-R-R-H-G-R-W-R spot 7   NH2-R-R-R-H-G-R-W-R-COOH
```

METHOD OF IDENTIFYING COMPOUNDS WHICH MODULATE HERPESVIRUS INFECTION

FUNDING STATEMENT

This work was supported by Public Health Service grants AI20530, AI27431 and AI30612. Therefore, the U.S. Government has certain rights in the invention.

BACKGROUND

Diseases caused by herpesviruses vary from mild to severe, and in some cases, infection with these viruses is life-threatening. Infected cell protein 4 (ICP4) is the major transcriptional regulatory protein of HSV-1. It is intimately involved in the control of viral gene expression during the course of infection. HSV-1 gene expression is regulated in an ordered fashion (Gu, B., et al., *Mol. Cell. Biol.*, 15:3618–3626 (1995); 24, 50), such that three phases of gene expression can be distinguished: the immediate early (IE), early (E), and late (L) genes (Honess, R. W., and Roizman, B., *Proc. Natl. Acad. Sci. USA.*, 72:1276–1280 (1975)). During this process, ICP4 acts as a negative regulator of IE gene expression as a positive transactivator of E and L gene expression (Courtney, R. J., and Benyesh-Melnick, M., *Virology*, 62:539–551 (1974); (Dixon, R. A. F. and Schaffer, P. A., *J. Virol.*, 36:189–203 (1980); (Kemp, B. E., et al., *J. Biol. Chem.*, 252:4888–4894 (1977); (Preston, C. M., *J. Virol.*, 29:275–284 (1979a); (Preston, C. M., *J. Virol.*, 32:357369 (1979b); Watson, R., and Clements, J. B., *Nature (London)*, 285:329–330 (1980)). Because of its role in activation, ICP4 is absolutely required for viral growth (Godowski, P. J. and Knipe, D. M., *Proc. Natl. Acad. Sci. USA*, 83:256–260 (1986); (Preston, C. M., *J. Virol.*, 29:275–284 (1979a)).

Genetic analyses of the functional organization of the ICP4 protein have shown the following: residues 143–210 and residues 800–1298 are required for transactivation (Paterson, T., and Everett, R. D., *Virology*, 166:186–196 (1988); Shepard, A. A., Imbalzano, A. N. and DeLuca, N. A., *J. Virol.*, 63:3714–3728 (1989)); residues 263–487 are required for DNA-binding (Shepard, A. A., Imbalzano, A. N. and DeLuca, N. A., *J. Virol.*, 63:3714–3728 (1989); Wu, C-L. and Wilcox, K. W., *J. Virol.*, 65:1149–1159 (1991)); residues 723–732 are required for nuclear localization (DeLuca, N. A., and Schaffer, P. A., *J. Virol.*, 62:732–743 (1988); Showalter, S. D., Zweig, M. and Hampar, B., *Infect. Immun.*, 34:684–692 (1981)); residues 309–489 including the DNA-binding domain are required for dimerization (Shepard, A. A., Tolentino, P. and DeLuca, N. A., *J. Virol.*, 64:3916–3926 (1990); Wu, C-L. and Wilcox, K. W., *Nucl. Acids Res.*, 18:531–538 (1990)); and residues 171–251 of ICP4 are important for its phosphorylation (DeLuca, N. A., and Schaffer, P. A., *J. Virol.*, 62:732–743 (1988)). Despite the extensive genetic analysis of the ICP4 gene, there is little information available about the phosphorylation on the molecule or its impact on infectivity.

Extensive research has been conducted to identify anti-herpesvirus agents for use in treating infection. For example, acyclovir and vidarabine inhibits viral DNA synthesis. However, vidarabine produces gastrointestinal and neurologic side effects and in some experimental models vidarabine has teratogenic, mutagenic and carcinogenic properties (Fields, B. N., et al., *Fields Virology*, 2nd ed., 1:448, Raven Press Publ. 1990). In addition, resistance of HSV to acyclovir develops readily in vitro and also occurs in vivo (Fields, B. N., et al., *Fields Virology*, 2nd ed., 1:450, Raven Press Publ. 1990). New medicaments and assays for identifying them are therefore desirable.

SUMMARY OF THE INVENTION

The present invention relates to a method of identifying a compound which modulates (enhances, inhibits, reduces) herpesvirus infection of a vertebrate cell comprising the steps of combining a phosphorylating enzyme capable of catalyzing the phosphorylation of ICP4, a substrate comprising a polypeptide which is phosphorylated by the enzyme, a phosphate source and the compound to be assessed; maintaining the combination under conditions appropriate for phosphorylation of the substrate; and determining phosphorylation of the substrate which occurs in the presence of the compound to be assessed.

The phosphorylating enzyme capable of catalyzing the phosphorylation of ICP4 can be, for example, an ICP4-associated kinase (e.g., ICP4, an enzymatically functional portion of ICP4 or a kinase activity closely associated with ICP4), protein kinase A, protein kinase C or casein kinase II. The substrate comprising a polypeptide which is phosphorylated by the enzyme can be, for example, all or a portion of isolated or recombinant ICP4 or ICP4tide. The phosphate source can be, for example, ATP or a derivative thereof.

In one embodiment, the present invention relates to a method of identifying a compound which modulates herpesvirus infection of a vertebrate cell comprising the steps of combining a phosphorylating enzyme capable of catalyzing the phosphorylation of ICP4, a substrate comprising a polypeptide which is phosphorylated by an ICP4-associated kinase, a phosphate source and the compound to be assessed; maintaining the combination under conditions appropriate for phosphorylation of the substrate; and determining phosphorylation of the substrate which occurs in the presence of the compound to be assessed.

In another embodiment, the present invention relates to a method of identifying a compound which modulates herpesvirus infection of a vertebrate cell comprising the steps of combining a phosphorylating enzyme which is capable of catalyzing the phosphorylation of ICP4, all or a portion of isolated or recombinant ICP4 which is phosphorylated by the enzyme, a phosphate source and the compound to be assessed; maintaining the combination under conditions appropriate for phosphorylation of the ICP4; and determining the amount of phosphorylation of the substrate which occurs in the presence of the compound to be assessed.

In another embodiment, the present invention relates to a method of identifying a compound which modulates herpesvirus infection of a vertebrate cell comprising the steps of combining a substrate comprising a polypeptide which is phosphorylated by an ICP4-associated kinase, all or a portion of an isolated or recombinant ICP4-associated kinase which is capable of catalyzing the phosphorylation of the substrate, a phosphate source and the compound to be assessed; maintaining the combination under conditions appropriate for phosphorylation of the substrate; and determining the amount of phosphorylation of the substrate which occurs in the presence of the compound to be assessed.

In a further embodiment, the present invention relates to a method of identifying a compound which modulates herpesvirus infection of a vertebrate cell comprising the steps of combining all or a portion of an isolated or recombinant ICP4-associated kinase which is capable of catalyzing the phosphorylation of ICP4, all or a portion of isolated or recombinant ICP4 which is phosphorylated by an ICP4-associated kinase, a phosphate source and the compound to be assessed; maintaining the combination under conditions appropriate for phosphorylation of the ICP4; and determining the amount of phosphorylation of the ICP4 which occurs in the presence of the compound to be assessed.

The present invention also relates to the compounds identified by the methods of the present invention. In addition, the invention relates to a method of modulating herpesvirus infection in a mammal comprising administering an effective amount of the compound identified by the methods of the present invention.

BRIEF DESCRIPTION OF THE FIGURES

FIG. 4 is the amino acid sequence of the serine-rich region (residues (142–210) (SEQ ID No: 1) of HSV-1 ICP4; the amino acid residues (SEQ ID NO: 3) marked with dots correspond to the N-terminal sequence of spot 7 of the phosphopeptide map described in Example 2.

DETAILED DESCRIPTION OF THE INVENTION

Figure 1:
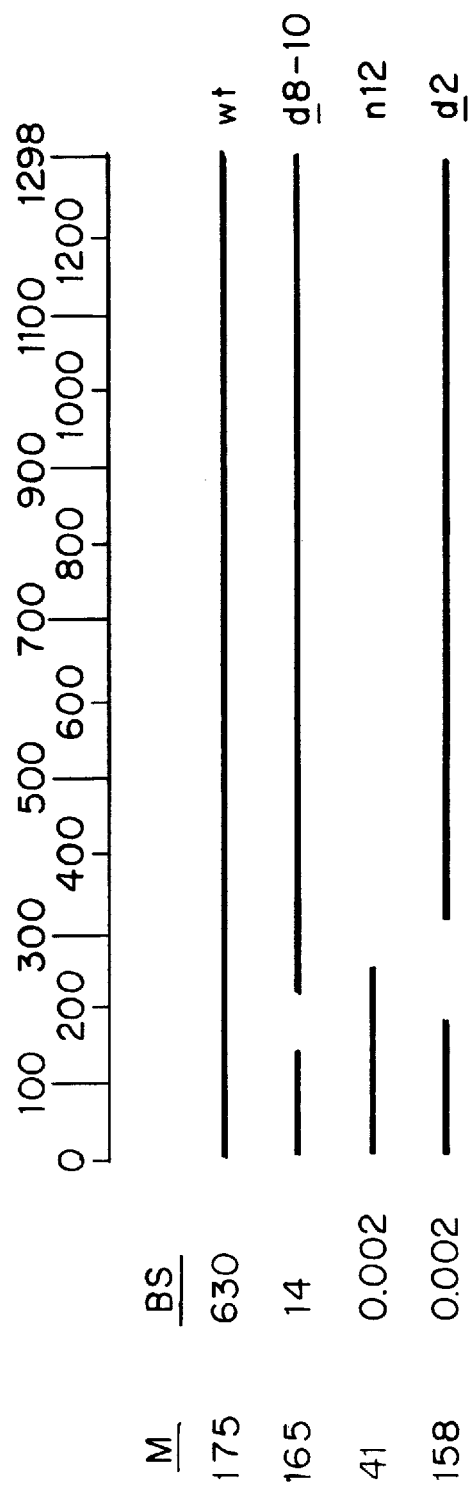
FIG. 1 is a schematic of the structures of ICP4 deletion (d) and nonsense (n) mutations used in this study, wherein the apparent molecular masses (M) of mutant peptides are shown in kilodaltons, and burst sizes (B.S.) are shown as PFU per Vero cell for each of the mutants and for the wild-type virus.

As described herein, purified herpesvirus infected cell protein 4 (ICP4), the major transactivator encoded by herpesvirus, has an associated protein kinase activity that phosphorylates ICP4 itself (i.e., an ICP4-associated kinase activity). That is, ICP4 has been found to be autophosphorylatable. This phosphorylation activates the protein molecule for other phosphorylation events and activation of late gene expression. The activity shows optimal activity under conditions different from the major host cell kinases and therefore is intrinsic to ICP4 or is a unique enzymatic kinase activity. The activity is not observed with a mutant ICP4 molecule d8-10, in which the serine rich region of the ICP4 molecule is deleted, providing further evidence that the activity is associated with ICP4. The herpesvirus mutant d8-10 is reduced for replication at least 50–100 fold in epithelial cells but more importantly, $10^4$ fold relative to wild type virus in sensory neurons. Therefore, this activity stimulates growth in epithelial cells but is especially important for viral growth in neuronal cells. Thus, for example, an inhibitor of the ICP4 protein kinase activity would reduce viral growth in epithelial cells but essentially block viral growth in sensory neurons and prevent viral entry or replication in the central nervous system and/or prevent viral reactivation from a latent infection.

Thus, the present invention is based on the discoveries of the autophosphorylation activity of ICP4 and that the serine rich region of the ICP4 or its phosphorylation stimulates phosphorylation of other sites on the ICP4 molecule. The invention is also based on the discovery of the significance of the serine rich region of the ICP4 protein in phosphorylation, as a site for cellular protein kinase A (PKA) and for growth of herpesvirus in vivo, particularly in sensory neurons.

Efficient expression of herpes simplex virus (HSV) genes requires the synthesis of functional ICP4, a nuclear phosphoprotein that contains a prominent serine-rich region between amino acids 142–210. Residues in this region are not only potential sites for phosphorylation but also are involved in the functions of ICP4. As described in Example 1, by comparing the growth of a virus deleted for this region (d8-10) with wild-type virus (KOS) in PC12 cells or PC12 cells that are deficient in cAMP-dependent protein kinase (PKA), two observations were made: (1) growth of wild-type virus was impaired by one to two orders of magnitude in the PKA-deficient cells, indicating the involvement of PKA in the growth cycle of HSV-1; (2) while the growth of d8-10 was impaired almost two orders of magnitude in wild-type cells, it was not further impaired (as was wild-type virus) in PKA-deficient cells, implicating the region deleted in d8-10 as a possible target for cellular PKA. In trigeminal ganglia of mice, the d8-10 mutant virus grew poorly; however, it established latency in nearly 90% of ganglia tested. Studies of the phosphorylation of wild-type and d8-10 ICP4 revealed that the serine-rich region is a major determinant for phosphorylation of ICP4 in vivo and the phosphorylation state could change as a function of the PKA activity. Consistent with this observation, the serine rich region of ICP4 was shown to be a target for PKA in vitro. While intact ICP4 was readily phosphorylated by ICP4 in vitro, the d8-10 mutant ICP4 was not. Moreover, a synthetic peptide representing a sequence in the serine tract that is predicted to be a substrate for PKA was phosphorylated by PKA in vitro, having a Km within the physiological range. These data demonstrate that PKA plays a role in viral growth through phosphorylation of one or more sites on the ICP4 molecule.

ICP4 has been shown to undergo phosphorylation in infected cells (Wettenhall, R. E. H., and Morgan, F. J., *J. Biol. Chem.*, 259:2084–2091 (1984); Wilcox, K. W., Kohn, A., Sklyanskaya, E. and Roizman, B., *J. Virol.*, 33:167–182 (1980)), and ADP-ribosylation (Preston, C. M. and Notarianni, E. L., *Virology*, 131:492–501 (1983)) and adenylation/guanylation (Blaho, J. A. and Roizman, B., *J. Virol.*, 65:3759–3769 (1991)) in isolated nuclei or nuclear extracts. The only biochemical evidence available regarding ICP4 phosphorylation is that a ts mutant form of ICP4 labeled at the nonpermissive temperature contained phosphoserine and phosphothreonine residues (Faber, S. W. and Wilcox, K. W. *Archives of Virol.*, 91:297–312 (1986)). As many as three species of ICP4 are resolved by SDS-PAGE (Pereira, L., Wolff, M. H., Fenwick, M. and Roizman, B., *Virology*, 77:733–749 (1977)), and as many as seven species are resolved by two-dimensional isoelectrofocusing (Ackermann, M., Braun, D. K., Pereira, L. and Roizman, B., *J. Virol.*, 52:108–118 (1984)). The precise nature of the post-translational modifications of ICP4 and the origin of this heterogeneity have not been described, but these modifications may regulate the activities of ICP4 (Michael, N., Spector, D., Mavromara-Nazos, P., Kristie, T. M. and Roizman, B., *Science*, 239:1531–1534 (1988); Papavassiliou, A. G, Wilcox, K. W. and Silversrein, S. J., *EMBO J.*, 10:397–460 (1991); Rice, S. A. and Knipe, D. M., *J. Virol.*, 62:3814–3823 (1988); Su, L., and Knipe, D. M., *Virology*, 170:496–504 (1989)).

Residues 175–198 of ICP4 comprise a serine-rich region that is conserved among the ICP4 homologs and contains 19 serine residues and 1 threonine residue in a 24-residue sequence. This region also contains consensus sites by cellular protein kinase A (PKA), protein kinase C (PKC), and casein kinase II (CKII). To define the complexity of the sites of phosphorylation and to initiate mapping of the site(s) of phosphorylation of ICP4, two-dimensional phosphopeptide mapping of wild type and mutant forms of ICP4 labeled in infected cells or in vitro has been performed and is described in Example 2. Wild type ICP4 labeled in infected cells shows a complex pattern of phosphopeptides, and smaller mutant forms of ICP4 show progressively fewer phosphopeptides, arguing that the multiple sites on ICP4 are phosphorylated. The serine-rich region of ICP4, residues 175–198, was shown to be a site for phosphorylation. Furthermore, the serine-rich region or the phosphorylation of this region increases phosphorylation of all phosphopeptides. A mutant ICP4 molecule lacking the serine-rich region showed low levels of phosphorylation by PKA or PKC in vitro. These results suggest that there may be a sequential phosphorylation of ICP4 with the serine-rich region stimulating phosphorylation of the rest of the molecule. In addition, purified ICP4 showed an associated kinase activity or an autophosphorylation activity with properties different from PKA or PKC.

In accordance with these discoveries, the present invention relates to a method of identifying a compound that modulates herpesvirus infection in a vertebrate cell comprising the steps of combining a phosphorylating enzyme capable of catalyzing the phosphorylation of ICP4, a substrate comprising a polypeptide which is phosphorylated by the enzyme, a phosphate source and the compound to be assessed; maintaining the combination under conditions appropriate for phosphorylation of the substrate; and determining phosphorylation of the substrate which occurs in the presence of the compound to be assessed.

As used herein the term "modulates" includes inhibition, reduction or enhancement of herpesvirus infection. The methods of the present invention are used to identify compounds which modulate herpesvirus infection in vertebrate cells, particularly mammalian cells (e.g., human cells, equine cells, bovine cells).

The phosphorylating enzyme is an enzyme capable of catalyzing the phosphorylation of ICP4, such as ICP4, an enzymatically functional portion of ICP4, a kinase closely associated with ICP4, protein kinase A (PKA), protein kinase C (PKC) or casein kinase II (CKII). The phosphorylating enzyme can act in a trans configuration (e.g., ICP4, an enzymatically functional derivative or portion of ICP4, PKA, PKC, or CKII) or in a cis configuration (e.g., ICP4). As used herein the term "enzymatically functional derivative or portion of ICP4" refers to a derivative or portion of ICP4 which phosphorylates ICP4.

The substrate for use in the methods of the present invention is a substrate which comprises a polypeptide which is phosphorylated by the enzyme. For example the substrate can be ICP4. In addition, derivatives or portions of ICP4 or synthetic peptides which correspond to phosphorylation sites of ICP4, such as the ICP4tide described in Example 1, can be used as substrates in the methods of the present invention. Other synthetic peptides can be prepared for use in the methods of the present invention using known techniques.

The term "ICP4" includes the herpes simplex virus (HSV) ICP4 protein and fragments, homologs and derivatives of the HSV ICP4 protein. For example, fragments of the herpes simplex virus type 1 (HSV-1) ICP4 protein that can be used in the present invention include residues 1–777, residues 1–592, residues 1–251, residues 171–251, residues 142–210, residues 175–198, and residues 165–179 of ICP4. Homologs of the ICP4 protein include for example, herpes simplex virus type 2 (HSV-2) ICP4, varicella zoster virus (VZV) 140K immediate early protein (Davison, A. J., et al., *J. Gen. Virol.*, 66:207–210 (1985)), pseudorabies (PrV) immediate early protein (Cheung, A. K., *Nucleic Acids Res.*, 17:4637–4646 (1989)), Marek's disease virus ICP4 (Anderson, A. S., et al., *Virol.* 189:657–667 (1992)), equine herpes virus type 1 immediate early protein (Grundy, F. J., et al., *Virol.*, 172:223–236 (1989)) and bovine herpes virus type 1 immediate early BICP4 protein (Schwyzer, M. C., et al., *Virol.*, 197:349–357 (1993)). Derivatives of the ICP4 protein include, for example, ICP4 protein which has been modified resulting in an ICP4 protein with similar or enhanced enzymatic and/or substrate properties. Such modifications include alteration of the amino acid sequence of the ICP4 protein wherein one or more amino acids encoding the ICP4 protein has been added, deleted or substituted using known techniques resulting in a modified ICP4 protein with similar or enhanced enzymatic and/or substrate properties. Assessment of derivatives of ICP4 for similar or enhanced enzymatic and/or substrate properties are performed using known techniques. To optimize the results obtained, cofactors and/or coenzymes for the reaction can be added as needed.

The ICP4 of the present invention can be isolated, chemically synthesized or recombinantly produced. For example, ICP4 for use in the present invention can be isolated from cells infected with herpesviruses, such as HSV-1, HSV-2, VZV, PrV, Marek's disease virus, equine herpes virus type 1 and bovine herpes virus type 1. In addition, based upon the genetic analysis of ICP4 provided in the literature, the ICP4 for use in the methods of the present invention can be chemically synthesized or produced using recombinant or genetic engineering techniques well known in the art. An example of the preparation of a synthetic peptide corresponding to the PKA phosphorylation site in the serine rich region of ICP4 is provided in Example 2.

The phosphate source is any suitable compound which can donate one or more phosphate groups in the methods of the present invention. For example, the phosphate source can be ATP or derivatives thereof.

Any suitable procedure can be used to determine phosphorylation of the substrate. Example 2 describes one method, SDS PAGE analysis of the reaction, which can be used to determine phosphorylation of the substrate in the methods of the present invention. In addition, an immunoprecipitation method can be used to determine phosphorylation of the ICP4 protein. Alternatively, phosphorylation of the substrate can be determined by binding labeled phosphopeptides to phosphocellulose paper. For example, the ICP4tide peptide can be labeled in an incubation with purified ICP4 and bound to phosphocellulose paper, wherein the paper is counted to determine the amount of label bound to the peptide (which is bound to the phosphocellulose paper). In addition, trichloroacetic acid prepicipitation of the reaction can be performed to determine phosphorylation of the ICP4 protein.

In the method of the present invention, the compound to be assessed is combined with a phosphorylating enzyme capable of catalyzing the phosphorylation of ICP4 and a substrate comprising a polypeptide which is phosphorylated by the enzyme, and the combination is maintained under conditions appropriate for phosphorylation of the substrate. The reaction mixture in the methods of the present invention can be combined and treated in a variety of ways.

For example, when ICP4 is the phosphorylating enzyme, about 5 ng to about 50 ng ICP4, wherein the preferred amount is about 20 ng purified ICP4 protein, is combined with the compound to be assessed. In this embodiment, the buffer conditions can be about 10 mM Tris, 10 mM MgCl$_2$, 50 mM NaCl, 10 mM DTT and 20 $\mu$M (0.15 mCi) [$\gamma$-$^{32}$P]ATP.

When ICP4 is the substrate and PKA is the phosphorylating enzyme, about 5 ng to about 50 ng ICP4, wherein the preferred amount is about 20 ng purified ICP4 protein, and about 10 U to about 300 U PKA, wherein the preferred amount is about 60 U PKA is combined with the compound to be assessed. In this embodiment, the buffer conditions can be about 10 mM Tris, 10 mM MgCl$_2$, 50 mM NaCl, 10 mM DTT and 20 $\mu$M (0.15 mCi) [$\gamma$-$^{32}$P]ATP.

When ICP4 is the substrate and PKC is the phosphorylating enzyme, about 5 ng to about 50 ng ICP4, wherein the preferred amount is about 20 ng purified ICP4 protein, and about 10 U PKC to about 300 U PKC, wherein the preferred amount is about 75 U PKC, is combined with the compound to be assessed. In this embodiment, the buffer conditions can be about 10 mM MgCl$_2$, 1mM CaCl$_2$, 100 mg/ml phosphatidylserine, 6 $\mu$g/ml diolein and 20 mM (0.15 mCi) $\gamma$-$^{32}$P]ATP.

The reaction mixture in the methods of the present invention can be incubated at about 25° C. to about 37° C., wherein the preferred temperature is about 30° C., for about 15 minutes to about 120 minutes, wherein the preferred time is about 30 minutes. Phosphorylation of the substrate which occurs in the presence of the compound to be assessed is then determined, quantitatively or qualitatively. In addition, the order in which the different components are combined for use in the methods of the present invention can vary depending on the assay conditions chosen. That is, the individual components used in the methods of the present invention can be added simultaneously or sequentially. Further, the conditions described above can be modified as necessary by a person of skill in the art. That is, the amounts of the components in the methods described herein are relative and can be scaled up or down, as appropriate.

The method of the present invention is useful for determining compounds which modulate phosphorylation of ICP4 and therefore, modulate herpesvirus infection of a vertebrate cell. Thus, the method of the present invention is useful to identify compounds which inhibit or enhance herpesvirus infection in a vertebrate cell. An inhibitor of herpesvirus can be used to prevent herpesvirus infection in mammals (e.g., in a prophylactic antiviral formulation) or to treat herpesvirus infections in mammals (e.g., herpetic infections such as herpetic stromal keratitis, encephalitis, genital herpes, disseminated neonatal infection, meningitis or pneumonia). An enhancer of herpesvirus can be used as a means of therapy for tumors such as malignant human gliomas (Martuza, R. L., et al., *Science*, 252:854–856 (1991), the contents of which are incorporated by reference.). The compounds identified by the methods of the present invention can be further assessed in anti-viral assays or in animal models. The compounds identified using the methods described herein can also be used to modulate herpesvirus infection in a mammal by administering an effective amount of the compound to the mammal. As used herein, an "effective amount" is that amount which will significantly modulate the herpesvirus infection in a vertebrate (e.g., mammal).

Those skilled in the art will understand that dosage can be optimized using standard procedures. In general, the compositions of the present invention are formulated in suitable pharmaceutically acceptable carriers and administered (e.g., by topical, oral or intravenous, intravaginal, subcutaneous, intramuscular or intradermal injection) at a dosage which is determined using known methods. The dosage is determined on an individual basis and will be based, at least in part, on consideration of the mammal's size, the disease, the severity of the symptoms to be treated, the result sought and other variations among hosts, etc. Thus, the dosage can be determined by one of ordinary skill in the art employing such factors and using no more than routine experimentation.

The following examples are provided to illustrate the invention, not to limit it. Those skilled in the art will understand that the specific constructions provided below may be changed in numerous ways, consistent with the above described invention while retaining the critical properties of the invention.

EXEMPLIFICATION

Example 1

Role of Protein Kinase A and the Serine-Rich Region of HSV-1 ICP4 in Viral Replication The following materials and methods were used in the experiments described below.

Viruses and Cells. The KOS strain of HSV-1 was used as the wild-type virus (DeLuca, N. A., et al., *J. Virol.*, 52:767–776 (1984)). The procedures for the propagation and plaque assay of KOS on Vero cells (an African green monkey kidney cell line) were as described previously (Dixon, R. A. F. and Schaffer, P. A., *J. Virol.*, 36:189–203 (1980)). The HSV-1 ICP4-deficient viruses n12, d2 (DeLuca, N. A. and Schaffer, P. A., *J. Virol.*, 62:732–743 (1988)) and d8-10 (Shepard, A. A., et al., *J. Virol.*, 63:371 4–3728 (1989)) were propagated on E5 cells, a Vero-derived cell line that expresses complementing levels of the wild-type ICP4 upon infection (DeLuca, N. A., et al., *J. Virol.*, 56:558–570 (1985); DeLuca, N. A., and Schaffer, P. A., *J. Virol.*, 62:732–743 (1988)). The primary structures of the ICP4 molecules expressed from the above viruses are represented in FIG. 1. PC12 cells (a rat adrenal pheochromocytoma cell line) and PC12-derived cellular protein kinase A-deficient cell lines, A123.7 and AB11 (Ginty, D. D., et al., *J. of Bio. Chem.*, 266:15325–15333 (1991)), were grown in Dulbecco's modified Eagle's medium (DMEM) containing 0.45% glucose, 0.03% L-glutamine and 0.025% NaHC03, supplemented with: 10% fetal bovine serum and 5% horse serum in a humidified 10% CO$_2$ environment. A123.7, and AB11 cells, as well as the parental PC12 cell line were kindly provided by Drs. J. Wagner and D. Ginty (Harvard Medical School, Boston, Mass.). Media were changed every 2–3 days, and cells were harvested and subcultured once a week.

Virus yield assays. Approximately 5×10$^5$ cells in 35 mm petri dishes were infected at an moi of 5 PFU per cell in 0.1 ml for 1 h at 37° C. Following incubation, the monolayers were washed 3 times with medium and incubated with 3 ml medium for 18 h. Infected cell monolayers were then harvested, and clarified lysates were assayed on either Vero or E5 cells, a Vero-derived cell line that expresses complementary levels of wild type ICP4 upon HSV infection (DeLuca, N. A., et al., *J. Virol.*, 56: 558–570 (1985)), to determine the total virus yield. Burst sizes for the individual viral strains were expressed as PFU per infected cell.

Radioactive labeling of viral proteins. The medium for labeling infected cell proteins with [$^{35}$S] methionine consisted of methionine-free DMEM (Flow Laboratories) supplemented with 2% inactivated fetal bovine serum. Labeling medium for $^{32}$P was phosphate-free DMEM supplemented with 2% inactivated fetal bovine serum. Cells to be labeled with $^{32}$P were incubated in the phosphate-free medium for 4–5 hours prior to labeling. During radiolabeling, the cells were incubated at 37° C. in 2 ml of the appropriate medium containing either [$^{35}$S]methionine (20 μCi/ml) or carrier-free $^{32}$P-orthophosphate ($^{50}$ μCi/ml) (New England Nuclear Corp., Boston, Mass.). The time period for $^{32}$P labeling was normally 2.5–5.5 hours postinfection, 6–9 hours postinfection in cycloheximide reversal experiments, and 2–12 hours post-infection for the purification of the radiolabeled ICP4. At the end of the labeling, cells were washed four times in either phosphate-buffered saline or Tris-buffered saline containing both protease inhibitors TLCK (0.1 mM) and leupeptin (0.5 mg/ml) and phosphatase inhibitors sodium orthovanadate (0.1 mM) and sodium pyrophosphate (5 mM). Cells were then scraped into the solution and stored as decanted pellets at −80° C. For cycloheximide reversal experiments, 1×10$^6$ Vero cells were preincubated for 60 min in phosphate-free medium containing cycloheximide (100 μg/ml) and then infected with the wild-type or mutant viruses at an moi of 10 PFU per cell. After a 1 h adsorption period, phosphate-free medium containing 100 μg/ml cycloheximide was added, and the cultures were incubated at 37° C. for an additional 5 h. The cells were then washed three times with phosphate-free medium containing 10 μg/ml actinomycin D, and incubated with 100 μCi $^{32}$P-orthophosphate in 2 ml phosphate-free medium plus 10 μg/ml actinomycin D for additional 3 h. After incubation, the cells were washed with ice-cold PBS containing 0.1 mM TLCK and harvested directly in SDS sample buffer.

Purification of $^{32}$P-labeled ICP4. Both wild-type and mutant ICP4 proteins were isolated as previously described (Imbalzano, A. N., et al., *J. Virol.*, 64:2620–2631 (1990)) with minor modifications. Briefly, approximately 2×10$^8$ Vero cells were infected with wt or d8-10 virus at an moi of 10 PFU per cell and then labeled with 0.5 mCi of carrier-free $^{32}$P-orthophosphate from 2 to 12 h post-infection. The cells were harvested and subjected to homogenization for the isolation of nuclei as previously described (Imbalzano, A. N., et al., *J. Virol.*, 64:2620–2631 (1990)). The nuclei were then lysed in a buffer containing 50 mM Tris-HCl (pH 8.0), 0.5M KCl, 2% NP-40, 0.1 mM TLCK. The lysate was cleared by centrifugation for 1 h at 45,000 rpm in an SW50.1 rotor at 4° C. The supernatant was saved as the nuclear extract and subsequently fractionated on the basis of the size in a manner similar to that reported previously (Shepard, A. A. and DeLuca, N. A., *J. Virol.*, 65:299–307 (1991a)). The extract was applied to a 52×2 cm FPLC gel filtration column packed with Superose 6 (Pharmacia, Piscataway, N.J.), equilibrated with CBO.5 buffer [20 mM Tris-HCl (pH 8.0), 0.5 M KCI, 1 mM EDTA, 10 mM b-mercaptoethanol, 0.01% CHAPS, 0.1 mM TLCK) and run at a rate of 0.2 ml/min. Fractions were assayed by dot immunoblot (Imbalzano, A.N., et al., *J. Virol.*, 64:2620–2631 (1990)). ICP4-containing fractions were pooled and further fractionated by chromatography over a 1 ml mono Q anion-exchange FPLC column (Pharmacia, Piscataway, N.J.) at a rate of 1 ml/min and eluted with a 50 mM to 0.5 M KCI gradient. Again, the peak fractions were pooled and further purified on a specific DNA-binding affinity column which was constructed using the oligonucleotides previously described (Imbalzano, A. N., et al., *J. Virol.*, 64:2620–2631 (1990)) by the method of Kadonaga and Tjian (Kadonaga, J. T., and Tjian, R. *Proc. Natl. Acad. Sci. USA.*, 83:5889–5893 (1986)). Following this procedure, a single polypeptide band was observed in Coomassie blue stained SDS-polyacrylamide gels.

In vitro phosphorylation reactions i) In vitro phosphorylation of purified ICP4 proteins with PKA. Approximately 20 ng of the purified ICP4 protein was added to a solution containing 10 mM Tris (pH 7.2), 10 MM MgCl$_2$, 50 mM NaCl, 10 mM DTT and 20 mM (0.15 mCi) [γ$^{32}$P]ATP. The phosphorylation reaction was initiated by adding 60 U of protein kinase A type I catalytic subunit purified from bovine heart (Sigma Chem. Co, 1000U/0.016 mg protein). Reaction mixtures were incubated at 30° C. for 30 min and stopped by addition of SDS-sample buffer. Equal amount of aliquots were analyzed by SDS-PAGE and transferred onto a nitrocellulose sheet for exposure to Kodak X-AR film and for staining with an ICP4-specific antibody.

ii) In vitro phosphorylation of a synthetic peptide. A peptide containing a potential protein kinase A site in the serine-rich region of ICP4 (RRRRHGRWRPSASST, residues 165–179) (SEQ ID NO: 2 ) was synthesized on an Applied Biosystems model 430A automated peptide synthesizer and purified by HPLC. Amino acid analysis confirmed the authenticity of this peptide, termed ICP4tide. ICP4tide (100 μM), or Kemptide (LRRASLG, Sigma Inc.), a commercially available substrate for protein kinase A (100 mM), was then incubated at 30° C. in a solution containing 24 mM MES (pH 7.0), 60 mM ATP, 5.6 nM [$^{32}$P]ATP (300–600 Ci/mmol). Each reaction was subsequently initiated by adding 80 U of protein kinase A type I catalytic subunit purified from bovine heart (Sigma Chem. Co., 1000U/0.016 mg protein) to a final volume of 52.5 μl. Following incubation for 4 minutes, 20 μl of the reaction was spotted onto P81 phosphocellulose strips, and phosphopeptides were quantitated after washing three times in 10 μl of 75 mM phosphoric acid as previously described (Roskoski, R. Jr., *Methods in Enzymology*, 99:3–6 (1983)). For kinetic studies, the concentration of ICP4tide was varied as indicated. The ICP4tide was also phosphorylated in a manner similar to those described below for phosphorylation of purified ICP4 proteins with PKA except that synthetic peptide replaced the purified ICP4 and the ATP concentration was increased to 60 mM. Such phosphorylated peptides were resolved in a 27% SDS-polyacrylamide gel.

Protein Analysis i) SDS-PAGE. The harvested cell pellets were lysed in sodium dodecyl sulphate (SDS)-containing sample buffer [62.5 mM Tris-HCI (pH 6.8), 2.3% (w/v) SDS, 10% glycerol, 5.0% (v/v) b-mercaptoethanol, 0.00125% (w/v) bromophenol blue]. The extracted viral polypeptides or purified ICP4 proteins suspended in SDS-sample buffer were analyzed by SDS-polyacrylamide gels cross-linked with diallytartardiamide (DATD) as described by Laemmli (Laemmli, U. K., *Nature (London)*, 277:680–685 (1970)) and modified by Gibson and Roizman (Gibson, W. and Roizman, B., *J. Virol.*, 10:1044–1052 (1972)). Where appropriate, the separated polypeptides were either stained with 0.25% Coomassie brilliant blue (Eastman, R250) or silver stained according to the protocol of the manufacturer (Bio-Rad Laboratories, Richmond, Calif.) and/or exposed to Kodak XAR film.

ii) Western immunoblot analysis. Separated polypeptides were electrophoretically transferred from gels onto nitrocellulose filters in a transfer apparatus according to the procedures of the manufacturer (Bio-Rad Laboratories, Richmond, Calif.). ICP4 polypeptides were visualized by probing filters with a 1:500 dilution of N15 polyclonal antibody directed against the N-terminal half of the ICP4 molecule. The primary antibody was detected by a 1:7500 dilution of secondary anti-rabbit immunoglobulin G (IgG) conjugated with alkaline phosphatase as indicated by the manufacturer (Promega Biotech, Madison, Wis.).

iii) Two-dimensional IEF. Two-dimensional isoelectrofocusing gel electrophoresis (2-D IEF) was performed using the Bio-Rad minigel system as prescribed by the manufacturer with some modifications. Briefly, the radiolabeled cell pellets were lysed, and the released polypeptides were solubilized in an urea-ampholine solution (pH 4-9 or pH 3-10) containing 2% CHAPS (Bio-Rad). The tube gels were pre-electrophoresed at 200 V, 300 V and 400 V for 15 min. each, and then washed carefully with chamber solutions (the upper chamber solution is degassed 20 mM NaOH, while the lower chamber solution is 10 mM $H_3PO_4$). Approximately 1.5–6 μg solubilized polypeptides were loaded onto the tube gels, and the electrophoresis was conducted from the base to the acid for a total of 5000 volt-hours. After equilibration in SDS sample buffer, the tube gel was placed horizontally over a stacking gel and overlaid with SDS sample buffer containing 1% agarose to fix the tube gel for electrophoresis in the second dimension. Electrophoresis was performed essentially as described above for the SDS-PAGE. After electrophoresis, the gel was fixed in the solution of $H_2$ methanol:acetic acid (6:3:1), dried and exposed to Kodak X-AR film for autoradiography.

Marker rescue and viral DNA analysis. Approximately $10^6$E5 cells were cotransfected with 1 μg of d8-10 viral DNA and 1 μg of BamHI-digested plasmid containing a BamHI Y fragment of the wild-type HSV-1 DNA using the calcium phosphate coprecipitation procedure (DeLuca, N. A., et al., *Mol. Cell. Biol.*, 5:1997–2008 (1985)). Because the genome of d8-10 contains a specific deletion of the serine-rich region in both copies of the ICP4 gene and it results in a partial ts mutant phenotype, plaque assays of the harvested viral particles were, therefore, conducted at both 39.6° C. and 37° C. Normal sized plaques at 39.6° C., indicative of reintroduction of wt sequences into the ICP4 gene, were isolated and subsequently plaque purified. The identity of the ICP4 allele was confirmed by Southern blot analysis (DeLuca, N. A., and Schaffer, P. A., *Nucleic Acids Res.*, 15:4491–4511 (1987)).

Animal studies. The mouse eye model was used to compare the in vivo growth characteristics of d8-10 and KOS. The procedures for the inoculation of the mouse corneas, the assays for virus replicating at the site of inoculation and in the trigeminal ganglia, as well as the determination of reactivatable latent virus were as previously described (Leib, D. A., et al., *J. Virol.*, 63: 759–768 (1989)).

THE CONTRIBUTION OF THE SERINE-RICH REGION OF ICP4 IN VITRO AND IN VIVO.

To investigate the role of the highly conserved serine-rich region, a mutant virus, d8-10 (Shepard, A. A., et al., *J. Virol.*, 63:371 4–3728 (1989)), which is deleted for the entire serine-rich region between amino acids 142–210 of ICP4 (FIG. 1), was studied. When the growth characteristics of d8-10 were examined in Vero cells, it was found that the virus was able to form plaques, although they were somewhat smaller than those of KOS, indicative of reduced virus yield. To quantify the growth deficiency of d8–10, both Vero and E5 cells were infected with KOS and d8-10 at an moi of 2.5 PFU per cell, and viral yields were determined by plaque assay on E5 cells. As shown in Table 1 below, KOS and d8-10 had comparable yields in E5 cells, although the burst size of d8-10 was significantly reduced in Vero cells, indicating that the region deleted in d8-10 is important for viral growth and that functional ICP4 expressed in E5 cells can complement the growth deficiency of d8–10. These results were consistent with the observations made by Paterson and Everett for a similar virus (Paterson, T., and Everett, R. D., *J. Gen. Virol.*, 71:1775–1783 (1990)).

TABLE 1

Growth of d8-10 in Vero and E5 Cells

| cells | virus | titer (pfu/ml) | burst size |
|---|---|---|---|
| Vero | KOS | $2.15 \times 10^8$ | 977 |
| | d8-10 | $3.10 \times 10^8$ | 14 |
| | r d8-10 | $1.85 \times 10^8$ | 841 |
| E5 | KOS | $1.95 \times 10^8$ | 886 |
| | d8-10 | $1.40 \times 10^8$ | 636 |
| | r d8-10 | $1.30 \times 10^8$ | 591 |

To determine if the growth deficiency was due solely to the deletion of the serine-rich region, a marker rescue experiment to reintroduce the deleted region into the ICP4 gene of the d8-10 genome was conducted. Monolayers of Vero cells were cotransfected with equal amount of infectious d8-10 viral DNA and a BamHI-digested plasmid containing the 1.84 kb BamHI Y fragment of HSV-1 DNA. The BamHI Y fragment possesses the sequence across the deleted codons. The d8-10 mutant virus forms significantly smaller plaques at 39.6° C. Normal sized plaques at 39.6° C. resulting from the plating of the transfection progeny on Vero cells were isolated, and the identity of the ICP4 allele was confirmed by Southern blot analysis. A representative rescuant was amplified and designated rd8-10. Vero cells and E5 cells were then infected with KOS, d8-10 and rd8-10, and the plaquing efficiency and burst size were determined as described above and are summarized in Table 1. As expected, rd8-10 had a similar burst size as wild-type virus. Taken together, the complementation of d8-10 in E5 cells (Table 1) and the marker rescue data together strongly suggested that the growth deficiency of d8-10 was due solely to the deletion of the serine-rich region. Therefore, although the serine-rich region of ICP4 is not essential for the viral growth in tissue culture, it does play a significant role in determining viral yield.

Figure 2:
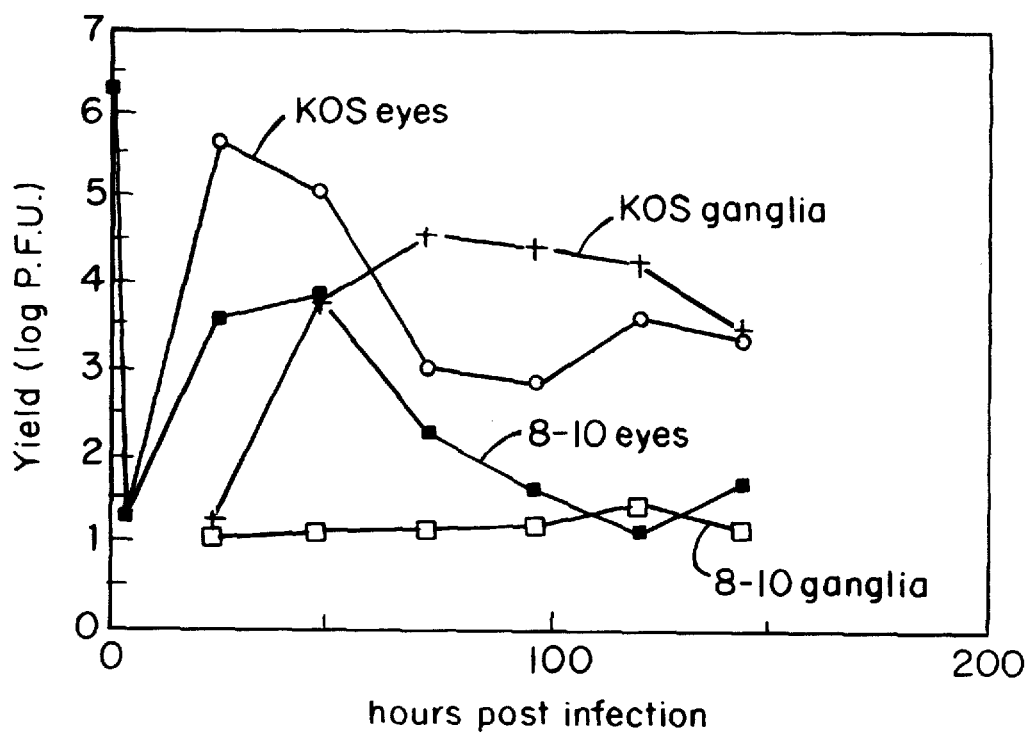
FIG. 2 is a graph of viral growth in both the eyes and the trigeminal ganglia of infected mice, monitored as a function of time post-infection by assay of PFU.

The serine-rich region is not essential for viral growth in tissue culture, but due to the conservation of this region in the neurotropic herpesviruses, it seemed reasonable to explore the possibility that this region may be important for the replicative cycle of HSV in vivo. Accordingly, d8-10 was introduced into mice by infection of the scarified corneas with an input dose of $2 \times 10^6$ PFU per eye. Viral growth at the site of inoculation and in trigeminal ganglia was then monitored by either eye swabs and by assay of PFU in ganglial homogenates as a function of time post-infection. FIG. 2 shows that d8-10 was able to grow but less efficiently than KOS in the eyes of the mice. This was consistent with the relative growth properties of KOS and d8-10 in cultured cells (Table 1). However, in the trigeminal ganglia, the growth of d8-10 was even more substantially impaired, suggesting that the serine-rich region of ICP4 is more important for growth in sensory neurons. The growth defect of d8-10 in the ganglia provided a basis for the conservation of the serine-rich region in the related alphaherpesviruses. The intact ganglia were also explanted at thirty days post-infection and cocultivated with E5 cells to determine the ability of d8-10 to establish latency and reactivate. As shown in Table 2 below, 16% of the explanted latent d8-10 ganglia reactivated on their own, and 89% of them could be reactivated in the presence of DMSO, a reagent that has been widely used to enhance the sensitivity of reactivation process (Whitby, A. J., et al., *Arch. Virol.*, 97:137–144 (1987)). Therefore, d8-10 was able to establish latency despite the apparent neuronal growth defect.

TABLE 2

| Virus | Reactivation (ganglia reactivated/total ganglia) | |
|---|---|---|
| | no addition | + DMSO |
| KOS (wild-type) | 12/12 (100%) | 9/9 (100%) |
| d8-10 | 6/38 (16%) | 8/9 (89%) |

Figure 3:
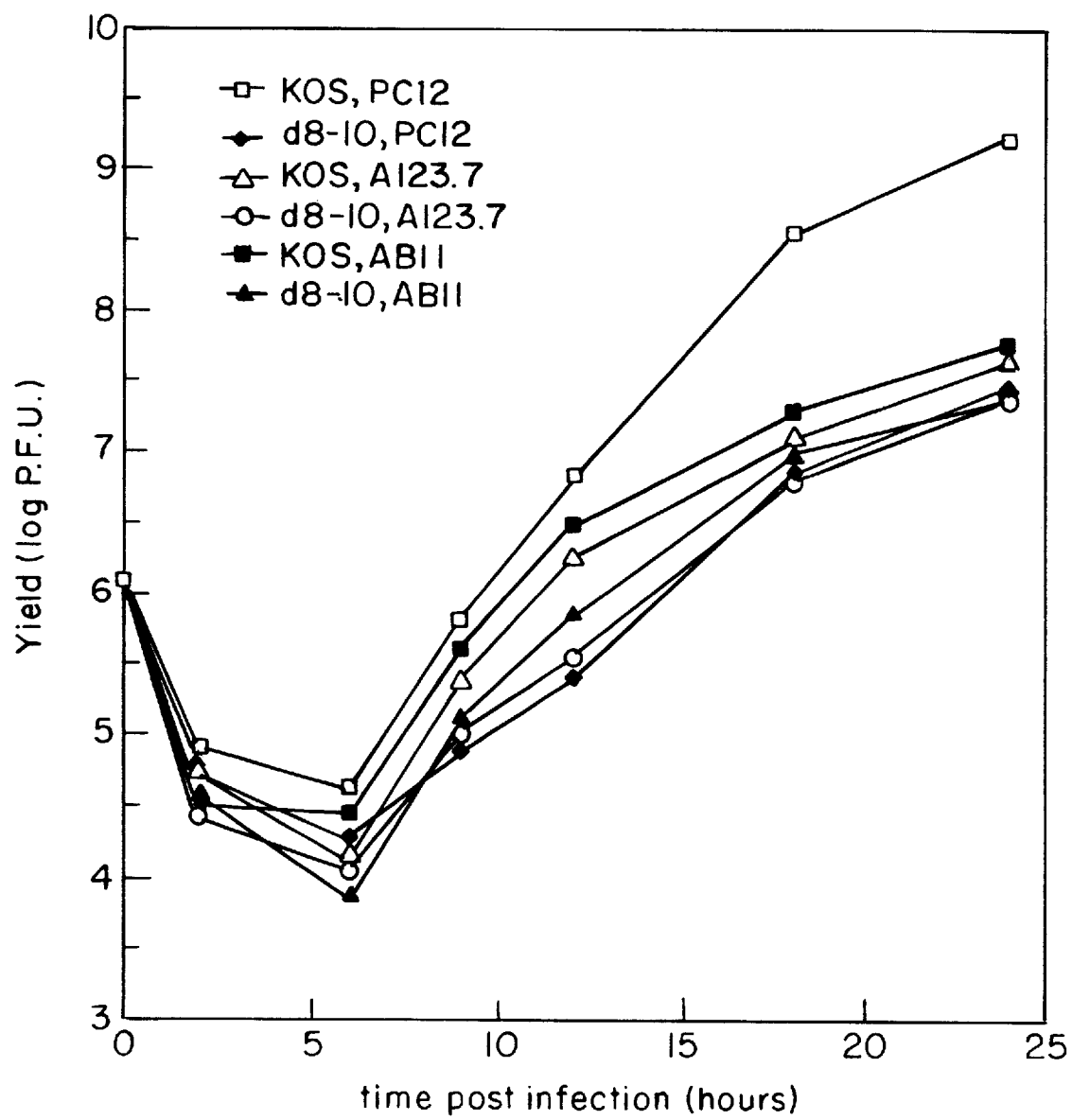
FIG. 3 is a graph of single-step growth curves of wild-type and d8-10 viruses.

The serine-rich region of ICP4 has been genetically implicated as a site for phosphorylation that is important for ICP4 activity and HSV growth. This raised the possibility that one or several kinases may regulate the activity of ICP4 and HSV growth by altering the modification state of the serine-rich region. Cellular protein kinase A (PKA) is a ubiquitous serine/threonine-specific kinase, and an ICP4 ts mutant protein is predominantly phosphorylated at serines and threonines (Faber, S. W., and Wilcox, K. W., *Archives of Virol.*, 91:297–312 (1986b)). Therefore, the possible involvement of PKA in ICP4 phosphorylation and HSV growth was studied. In the inactive state, PKA consists of a complex of two regulatory subunits and two catalytic subunits. Binding of cAMP alters the conformation of the regulatory subunits, causing them to dissociate from the complex. The released catalytic subunits are thereby activated to phosphorylate a variety of protein substrates that contain specific consensus motifs for PKA. Two PKA-deficient cell lines, AB11 and A123.7, have been described, which were derived from PC12 cells and created by transformation with a gene containing different point mutations in the regulatory subunits (Ginty, D. D., et al., *J. of Bio. Chem.*, 266:15325–15333 (1991)). These subunits cannot bind cAMP, and as a consequence, the catalytic subunits cannot be released and PKA remains inactive. The growth of d8-10 relative to wt virus in parental PC12 cells and PKA-deficient cells was tested in a single-step growth experiment. NGF-differentiated PC12 cells and PKA-deficient cells were infected in parallel in 35 mm plates with KOS and d8-10 at an moi of 2.5 PFU per cell. At the indicated times, the cells were scraped into the medium and sonicated and total virus was determined by plaque assay on E5 cells. The results (FIG.3) illustrate that although both KOS and d8-10 were able to grow in PC12 cells, the yield d8-10 was significantly lower (20- to 65-fold less) than that for KOS over the time course of the experiment. This was consistent with the observation on Vero cells (Table 1) and on BHK cells (Paterson, T., and Everett, R. D., *J. Gen. Virol.*, 71:1775–1783 (1990)). Interestingly, when the two different PKA-deficient cell lines were used for infection, the growth of wt was reduced to the level observed (one to two orders of magnitude) with the mutant d8-10 on normal PC12 cells. However, the growth of d8-10 was not further impaired in PKA-deficient cells relative to the growth in PC12 cells, implying that the deletion of the serine-rich region reduces the importance of PKA activity for d8-10 growth. This provides a connection between the serine-rich region of ICP4, the activity of cellular PKA, and HSV-1 growth. A simple explanation would be that the serine-rich region is a functional target for cellular PKA. A third PKA-deficient cell line A126 which was isolated following nitrosoguanidine mutagenesis to ensure that the growth difference was not due to the cell clonal variation was used. The use of these cells yielded similar results.

PHOSPHORYLATION OF THE SERINE-RICH REGION.

Previous studies have shown that ICP4 exists in cells as multiple forms possibly due to different phosphorylation states (Pereira, L., et al., *Virology*, 77:733–749 (1977); (Wilcox, K. W., et al., *J. Virol.*, 33:167–182 (1980)). Genetic analysis has implicated that the serine-rich region in the ICP4 molecule is one of the phosphorylation sites (DeLuca, N. A., and Schaffer, P. A., *J. Virol.*, 62:732–743 (1988)). Using different ICP4 mutant viruses, the phosphorylation patterns of the corresponding ICP4 polypeptides by SDS-PAGE were analyzed. Vero cells were infected with wild-type or ICP4 mutant viruses at an moi of 10 PFU per cell and metabolically labeled with [32P]-orthophosphate under cycloheximide reversal conditions. The crude cell extracts were separated by SDS-PAGE and subsequently transferred onto a nitrocellulose sheet. Whole cell lysates were solubilized in SDS, electrophoretically separated on a 9% polyacrylamide gel, and transferred onto nitrocellulose filter paper. The filter was exposed to XAR5 film to generate the autoradiogram shown. Following the exposure, the filter was probed with antibody against ICP4. $^{32}$P-labeled ICP4 proteins purified from KOS and d8-10 infected Vero cell extracts were electrophoretically separated in a 9% SDS-PAGE gel, also containing 1.0, 0.5, and 0.25 ug of β-galactosidase. The gel was stained with coomassie blue, dried, and exposed to XAR5 film.

The autoradiographic images of the labeled bands on the blot were made on Kodak XAR film prior to visualization of the ICP4 polypeptides with an ICP4-specific antibody to indicate the amount of proteins applied to each lane. This order of analysis was necessary because the labeled phosphate groups on the ICP4 polypeptides can be removed by alkaline phosphatase conjugated with the secondary antibody. As shown in FIG. 1, the n12 nonsense mutant virus (DeLuca, N. A., and Schaffer, P. A., *J. Virol.*, 62:732–743 (1988)) produced a truncated ICP4 molecule just long enough to include the serine-rich region. The stop codon in the n12 ICP4 gene is at codon 251. The ICP4 polypeptides expressed by n12 were highly phosphorylated and displayed several related migrating forms. The d2 deletion mutant virus specifies an ICP4 polypeptide lacking two-thirds of the serine-tract (Δ185–309, FIG. 1). Phosphorylation of the d2 ICP4 polypeptides was reduced dramatically compared to that of the wild-type ICP4 and the n12 ICP4.

To examine the differences in phosphorylation between the ICP4 proteins with or without the serine-rich region, [$^{32}$P]-labeled ICP4 proteins were purified from KOS and d8-10-infected Vero cell extracts. The amounts of purified proteins were then quantified on SDS polyacrylamide gel by using 1 μg, 0.5 μg, and 0.25 μg of β-galactosidase as standards. The gel was stained with Coomassie brilliant blue to indicate the amount of the d8-10 and the KOS ICP4 proteins. The same gel was also exposed to Kodak X-AR film, and the autoradiographic bands were scanned by densitometry. When a similar amounts of the ICP4 proteins were examined, the amount of phosphorylation on d8-10 ICP4 was 6 to 10 fold less than wt ICP4. These analyses strongly suggested that the serine-rich region is a major determinant for phosphorylation of ICP4. There are also other phosphorylation sites in the molecule because when this region was deleted as in d8-10, the ICP4 was still phosphorylated, albeit to a much lesser extent.

To further examine phosphorylation differences between the ICP4 proteins with or without the serine-rich region, the ICP4 molecules were examined by 2-D gel electrophoresis. Vero cells infected with wild-type or ICP4 mutant viruses were labeled with [$^{32}$P]-orthophosphate from 2.5 to 5.5 h post-infection. The whole cell lysates were solubilized in urea-containing ampholine solution and electrophoretically separated on acrylamide gels in the first dimension according to the corresponding points of isoelectrofocus (pIs) and the second dimension according to relative molecular weights. Electrophoresis in the first dimension was from base to acid on a scale of pH 9-4 or pH 10-3. The identity of labeled ICP4 proteins was confirmed by western blots. The wild-type ICP4 was heavily phosphorylated in Vero cells, and the phosphoproteins were highly heterogeneous with pIs ranging from approximately 7.8 to 5.5 and formed a series of at least eight spots (with [$^{35}$S]-labeled cell extracts, the 2-D IEF provides a better resolution of different species of the ICP4 proteins). The polypeptides in these spots appeared to differ in charge rather than apparent molecular weight, suggesting that they may be generated by either differential modifications or by the differential stability of phosphate groups on each molecule. Consistent with the previous 1-D gel analysis, the d8-10 ICP4, which lacks the entire serine-rich region, was greatly underphosphorylated and the distribution of isoforms was shifted toward more basic zones between 8.1 to 5.9; however, the n12 ICP4, which retains the serine-rich region, was extensively phosphorylated, and the pIs were very acidic ranging from 3.8 to 4.4. Thus, the results from the 2-D IEF analysis further indicated that the serine-rich region of ICP4 could serve as a major site for phosphorylation or promote phosphorylation of other regions of the molecule, or both. Like the wild-type ICP4, the mutant ICP4 polypeptides were also heterogeneous, and the polypeptides in these spots differed in charge. It should be pointed out that the measured pIs varied slightly from sample to sample, possibly due to the stability of phosphate groups on the molecules.

To more closely examine the effect of PKA on the modification of the serine-rich region of ICP4, the ICP4 from PC12-PKA-deficient cells were examined by 2-D gel electrophoresis. PC12 cells (WT) and PKA-deficient cells A123.7 (PKA$^-$) were infected with KOS and labeled with the indicated radioisotopes from 2.5 to 5.5 h post-infection. The whole cell lysates were subjected to 2-D IEF gel analysis. The parental PC12 and PKA-deficient cells infected with KOS or d8-10 were labeled with [$^{32}$P]-orthophosphate or [$^{35}$S]-methionine as described above. The resulting cell lysates were subjected to 2-D IEF to examine the phosphorylation of viral proteins as a function of the presence of PKA. The wild-type ICP4 proteins in PC12 cells again exhibited great heterogeneity with pIs ranging roughly from 7.7 to 5.8, forming a serine of at least eight spots clearly detected by [$^{35}$S]-methionine radioactivity. These results were basically consistent with the 2-D IEF gel analysis ICPs expressed in KOS virus-infected cells described above, and with the data obtained by Ackermann et al (Ackermann, M., et al., *J. Virol.*, 52:108–118 (1984)). The number of actual ICP4 species might be underestimated because of the limitations of the detection method and the insoluble material at the origin. In comparison, the distribution of different phosphorylated species of the wild-type ICP4 proteins from PKA-deficient cells shifted toward higher pIs between approximately 7.8 to 6.3 and certain relatively acidic spots were missing. These results were consistent with the notion of addition of fewer phosphate molecules onto the ICP4 protein when the activity of PKA is repressed.

$^{35}$S-methionine labeled cell extracts from d8-10 infected PC12 cells and PKA-deficient cells were also analyzed by 2-D IEF. PC12 cells (WT) and PKA-deficient cells A123.7 (PKA$^-$) were mock-infected or infected with d8-10. The infected cells were then labeled with [$^{35}$S]-methionine from 2.5–5.5 h postinfection, and then cell lysates were prepared and subjected to 2-D IEF. Due to the low level of phosphorylation of d8-10 ICP4 and the decreased resolution of $^{32}$P-labeled proteins on IEF, only the 35S-labeled d8-10 ICP4 gave interpretable results. No difference in phosphorylation states of the ICP4 proteins was apparent in the autoradiographic images of d8-10 infected cellular and viral protein patterns from PC12 cells and PKA-deficient cells. Therefore, the 2-D gel analysis strongly suggested that the cellular PKA was involved in the phosphorylation of ICP4 and the serine-rich region serves as an in vivo target for PKA.

IN VITRO PHOSPHORYLATION OF ICP4 BY PKA REQUIRES THE SERINE-RICH REGION.

To demonstrate directly that PKA can phosphorylate ICP4, native ICP4 proteins purified from cells infected with wt or mutant d8-10 virus were incubated with the catalytic subunits of PKA. ICP4 proteins purified from KOS or d8-10 infected Vero cells were incubated with [γ-$^{32}$P]-ATP in the presence of protein kinase A at 30° C. for 30 min as described in the text. The reaction products were resolved by SDS-polyacrylamide gel (9%) and transferred to a nitrocellulose filter paper for autoradiography and western blot analysis. Wild-type ICP4 protein was phosphorylated strongly by PKA, while with the same amount of protein used, d8-10 ICP4 showed little, if any, phosphorylation by PKA. Several bands were phosphorylated, and these were possibly contaminants associated with PKA. Thus, ICP4 containing the serine-rich region is a substrate for PKA in vitro, and the serine-rich region greatly stimulates phosphorylation by PKA.

Examination of the primary amino acid sequence of ICP4 proteins revealed a consensus motif for PKA phosphorylation in the serine-rich region. Accordingly, a peptide, named ICP4tide (RRRRHGRWRPSASST, residues 165–179) (SEQ ID NO: 2), corresponding to this potential site was synthesized and incubated in vitro with purified type I catalytic subunits of PKA and [γ-$^{32}$P]ATP. Kemptide (LRRASLG) (SEQ ID NO: 5), a commercially available substrate for PKA, was used as a positive control. Compared with Kemptide, ICP4tide was also strongly phosphorylated by PKA as shown in Table 3 below.

TABLE 3

Phosphorylation of ICP4tide

| Kinase | Peptide | Phosphorylation (cpm) | γ$^{32}$P incorporated (%) | Ratio** | Km (μM) |
|---|---|---|---|---|---|
| +PKA | Kemptide | 768687 | 26.1% | 88.5 | 9 |
|  | ICP4tide | 182104 | 6.2% | 26.2 | 38.96 |
| −PKA | Kemptide | 8682 | 0.3% |  |  |
|  | ICP4tide | 6946 | 0.24% |  |  |

**Ratio = $\frac{\text{Peptide} + \text{PKA}}{\text{Peptide} - \text{PKA}}$

*Km values were determined by linear regression analysis of the Lineweaver-Burk representation for the dependence of the reaction velocity on substrate concentration.

To determine the Km values of these reactions, we incubated different concentrations of ICP4tide with [Y-$^{32}$P]ATP and a fixed amount of PKA catalytic subunits (80 U each) for 4 min at 30° C. Varying amounts of ICP4tide were incubated with 60 U of PKA and 60 μM ATP, and the incorporation of $^{32}$P into ICP4tide was determined. From the Lineweaver-Burk representation of the data, the Km was determined as described (Michael, N., Spector, D., Mavromara-Nazos, P., Kristie, T. M. and Roizman, B., *Science*, 239:1531–1534 (1988)). The Km for Kemptide was 9 μM in our system (Table 3), which was similar to that reported previously (Michael, N., Spector, D., Mavromara-Nazos, P., Kristie, T. M. and Roizman, B., *Science*, 239:1531–1534 (1988);

Smith, C. A., Bates, P., Rivera-Gonzalez, R., Gu, B. and DeLuca, N. A., *J. Virol.*, 67:4676–4687 (1993)), while the Km for ICP4tide was 39 $\mu$M which was very comparable to those of physiological substrates of cellular PKA (Roskoski, R. Jr., *Methods in Enzymology*, 99:3–6 (1983)). Thus, the synthetic ICP4tide could be considered to be a good substrate for PKA in vitro. Additional studies demonstrated that the initial reaction rates at either the highest and lowest concentrations of substrate were in the linear range.

DISCUSSION

Growth properties of mutant viruses lacking the serine-rich region.

Previous studies have demonstrated that deletion of the conserved serine-rich sequence in the background of an ICP4 polypeptide truncated at residue 774 resulted in a loss of the ability to transactivate the early thymidine kinase gene promoter in transient assays (Shepard, A. A., et al., *J. Virol.*, 63:371 4–3728 (1989)). Paterson and Everett have also investigated the effect of mutations in the serine-rich region on the function of ICP4. They found that the deletion of the entire serine-rich region (codons 162 to 229) of ICP4 reduces the transactivation efficiency of the (gD) promoter in transient assays (Paterson, T., and Everett, R. D., *Virology*, 166:186–196 (1988a)) and delays the synthesis of early and late viral proteins in mutant virus-infected cells (Paterson, T., and Everett, R. D., *J. Gen. Virol.*, 71:1775–1783 (1990)). The growth efficiency of such mutant virus was also reduced more than 10-fold over a 24 h time course when tested on BHK cells (Paterson, T., and Everett, R. D., *J. Gen. Virol.*, 71:1775–1783 (1990)). The results of the growth and viral gene expression of d8-10 (deleted codons 142–210 of ICP4) in cultured cells described in Example 1 are consistent with those previous findings. The importance of the serine-rich region in viral growth was further demonstrated by tests in a mouse model, in which mice were infected with KOS or d8-10 on the corneas with an input dose of $2\times10^6$ PFU per eye. During acute infection in the eyes of the mice, the growth properties of d8-10 was similar to that seen in tissue culture. In contrast, viral growth in trigeminal ganglia was greatly decreased. However, these results demonstrate that the deleted serine-rich sequence does specify a function that is necessary for the activity of ICP4 and for the viral growth during a natural course of infection.

Phosphorylation of ICP4 polypeptides.

Many of the non-structural proteins encoded by HSV, such as ICP4 are phosphorylated in infected cells (Pereira, L., et al., *Virology*, 77:733–749 (1977); Wilcox, K. W., et al., *J. Virol.*, 33:167–182 (1980)). Wild-type and mutant forms of ICP4 are phosphorylated in a very complex manner and exhibit multiple electrophoretic forms on SDS gels (Preston, C. M., *J. Virol.*, 32:357369 (1979b); (Shepard, A. A. and DeLuca, N. A., *J. Virol.*, 65:299–307 (1991a); Shepard, A. A. and DeLuca, N. A., *J. Virol.*, 65:787–795 (1991b)). As described in Example 1, a major determinant for phosphorylation of ICP4 is localized to the prominent serine-rich region through genetic analysis and biochemical characterization. In addition it was determined that PKA can phosphorylate ICP4 as a function of the serine tract, in vivo and in vitro. Deletion of the serine-rich domain reduces the phosphorylation of ICP4 by at least ten fold as determined by analysis of ICP4 proteins in crude cell extracts, and it appears to reduce the phosphorylation by six to ten fold with the purified [$^{32}$P]-labeled proteins.

PKA has been reported to serve as a phosphate donor to correct a decreased mobility change of phosphorylated ICP4 polypeptides after dephosphorylation with phosphatases (Papavassiliou, A. G., et al., *EMBO J.*, 10:397–460 (1991)).

In the nucleus, PKA is known to associate with the transcriptional machinery and modify the activity of proteins that bind to DNA (Cherry, J. R, et al., *Cell*, 56:409–419 (1989); Ghosh, S., and Baltimore, D., *Nature (London)*, 344:678–682 (1990) (Luscher, B., et al., *Nature (London)*, 344:517–522 (1990); Riabowol, K. T., et al., *Nature (London)*, 336:83–86 (1988)). As further described in Example 1, the growth of wild-type virus in PKA deficient cells was reduced to the levels seen with d8-10 in PKA-proficient, and -deficient cells. This result provides genetic evidence that the serine tract is a functional target of PKA, and that interaction between PKA and ICP4 is important for optimum viral growth. It was also found that the presence of PKA in infected cells affected the isoelectric points of wild-type ICP4 on 2-dimensional gels, but had little effect on the d8-10 ICP4 protein. In vitro PKA phosphorylated wild-type ICP4 but was unable to phosphorylate the d8-10 protein. Moreover, a synthetic peptide (ICP4tide) representing a sequence in the serine tract that resembles a PKA phosphorylation site was phosphorylated by PKA, having a Km in the physiological range. Therefore, while PKA may influence many events in viral infection, the data presented herein show that PKA influences the activity of ICP4 by directly phosphorylating the serine-rich region.

Without being bound by any mechanism, the following is proposed. It is possible that different phosphorylation states of ICP4 could also affect its DNA-binding affinity to different viral promoters as previously proposed (Michael, N., et al., *Science*, 239:1531–1534 (1988); Papavassiliou, A. G., et al., *EMBO J.*, 10:397–460 (1991)). The negative charges resulting from phosphorylated serines and a threonine and from the adjacent eight acidic residues may together serve as a transactivation domain in a manner similar to the acidic regions identified in other eukaryotic transactivators (Hope, I. A., and Struhl, K., *Cell*, 46:885–894 (1986); Ptashne, M., *Nature*, 335:683–689 (1988)). Alternatively, alterations in the phosphorylation state may result in allosteric changes within ICP4 that alter protein-protein interactions with other cellular molecules. Such interactions would be important for the regulatory activity and hence the viral growth. The d8-10 ICP4 protein is reduced about 4-fold in the ability to form tripartite complexes on DNA with TBP and TFIIB (Smith, C. A., et al., *J. Virol.*, 67:4676–4687 (1993); Gu, B., et al., *Mol. Cell. Biol.*, 15:3618–3626 (1995)). While this is sufficient for the repressor activity of ICP4 (Gu, B., et al., *Mol. Cell. Biol.*, 15:3618–3626 (1995)), the reduction in the ability of d8-10 to activate transcription may be a consequence of its reduced ability to interact with the general transcriptional machinery. Therefore this region may be directly involved in the protein-protein interactions or regulate the affinity of the interactions. Recently, it has been shown that a 15 kd cellular coactivator, p15 (Kretzschmar, M., et al., *Cell*, 78:525–534 (1994)), or PC4 (Ge, H., and Roeder, R. G., *Cell*, 78: 513–523 (1994)) has striking amino acid similarity to the serine tract of ICP4 and is involved with the formation of tripartite complexes with TBP and, in this case, TFIIA (Kretzschmar, M., et al., *Cell*, 78:525–534 (1994)). It was found that the coactivator function of p15 was regulated by cellular kinases (Kretzschmar, M., et al., *Cell*, 78:525–534 (1994)). It may be that ICP4 is an activator and coactivator in one and that the function of ICP4 and the requirement for the serine tract may also depend on the abundance or state of cellular p15 in different cellular environments or as a consequence of external stimuli.

Example 2

Analysis of Phosphorylation Sites of the HSV-1 ICP4

The following materials and methods were used in the experiments described below.

Viruses and Cells. The KOS1.1 strain of HSV-1 was used as the wild-type virus (DeLuca, N. A., and Schaffer, P. A., *J. Virol.*, 62:732–743 (1988)). The procedures for the propagation and plaque assay of KOS 1.1 on Vero cells were as described previously (Knipe, D. M. and Spang, A. E., *J. Virol.*, 43:314–324 (1982)). The HSV-1 KOS ICP4-mutant viruses n12, d2, n214, and n208, (DeLuca, N. A., and Schaffer, P. A., *J. Virol.*, 62:732–743 (1988)) and d8-10 (Shepard, A. A., Imbalzano, A. N. and DeLuca, N. A., *J. Virol.*, 63:3714–3728 (1989)) were propagated on E5 cells, a Vero-derived cell line that expresses complementary levels of the wild-type ICP4 upon HSV infection (DeLuca, N. A., McCarthy, A. and Schaffer, P. A. *J. Virol.*, 56:558–570 (1985); DeLuca, N. A., and Schaffer, P. A., *J. Virol.*, 62:732–743 (1988)). The genotypes of the viruses are described in Table 4. The HSV-1 KOS1.1 d27 mutant virus was propagated on V27 cells (Rice, S. A., et al., *J. Virol.*, 63:3399–3407 (1989)).

TABLE 4

Genotype to virus strains used in this study

| Virus | IPC4 Gene | |
|---|---|---|
| wt | ICP4 gene with 1283 condons | — |
| d2 | Deletion of ICP4 gene codons 185–309 | DeLuca:, N. A., and Schaffer, P. A., J. Virol., 62:732–743 (1988) |
| d8-10 | Deletion of ICP4 gene codons 142–210 | Shepard, A. A., Imbalzano, A. N. and DeLuca, N. A., J. Virol., 63:3714–3728 (1989) |
| n208 | Nonsense codon at codon 777 of ICP4 gene | DeLuca, N.A., and Schaffer, P. A., J. Virol., 62:732–743 (1988) |
| n214 | Nonsense codon at codon 592 of ICP4 gene | DeLuca, N. A., and Schaffer, P. A., J. Virol., 62:732–743 (1988) |
| n12 | Nonsense codon at codon 251 of ICP4 gene | DeLuca, N. A., and Schaffer, P. A., J. Virol., 62:732–743 (1988) |

Labeling of viral proteins in infected cells and immunoprecipitation. Approximately $2 \times 10^6$ Vero cells were incubated in the phosphate-free DME medium (Flow Laboratory) containing 2% inactivated fetal bovine serum (FBS) 3 hours prior to infection. Cells were then infected with wild-type or mutant viruses at a multiplicity of infection (MOI) of 5 to 10 PFU per cell and labeled with 100 $\mu Ci^{32}P$-orthophosphate (New England Nuclear) in 2 ml of phosphate-free DMEM-2% FBS from 2.5–5.5 or -6.0 h postinfection. At the end of the labeling, cells were washed four times in phosphate-buffered saline containing the protease inhibitor TLCK (0.1 mM) and phosphatase inhibitors sodium orthovanadate (0.1 mM) and sodium pyrophosphate (5 mM). Washed cell pellets were either lysed in SDS-containing gel sample buffer [62.5 mM Tris-HCl (pH 6.8), 2.3% (w/v) SDS, 10% glycerol, 5.0% (v/v) 2-mercaptoethanol, 0.000125% (w/v) bromophenol blue] and directly subjected to SDS-gel electrophoresis or resuspended in 0.5 ml of lysis buffer (20 mM Tris-HCl pH 8.0, 150 mM NaCl, 1% NP40) containing 1 mM TLCK, 0.1 mM sodium orthovanadate and 5 mM sodium pyrophosphate for immunoprecipitation. For immunoprecipitation, the cell lysates were subjected to centrifugation in a microfuge for 15 minutes and portions of the solubilized lysate were incubated for 2–3 h at 4° C. with 3–4.5 $\mu$l of ICP4-specific monoclonal antibody 58S (IgG2a subclass) (Showalter, S. D., Zweig, M. and Hampar, B., *Infect. Immun.*, 34:684–692 (1981)) for wt, d2, and d8-10 virus-infected cell extracts or with polyclonal antibody N15 for n12, n214, and n208 virus-infected cell extracts. Different antibodies were used for the different ICP4 proteins because 58S is directed against an epitope in the carboxy-terminal portion of ICP4 (Showalter, S. D., Zweig, M. and Hampar, B., *Infect. Immun.*, 34:684–692 (1981)), while N15 recognizes the amino-terminal half of the molecule (Tseng, C., and DeLuca, N. A., unpublished results). At the same time, 80 $\mu$l Of Pansorbin cells (Calbiochem) were incubated with 5–10 $\mu$g of rabbit anti-mouse IgG2a for 1 h at 4° C. At the end of incubation, the excess antibody was washed away with lysis buffer. Immune complexes formed between ICP4 and ICP4-specific antibody were collected on rabbit anti-mouse IgG2a-conjugated Pansorbin cells for monoclonal antibody or on Pansorbin cells for polyclonal antibody by incubation for 1 h at 4° C. The immunoprecipitates were washed three times with phosphate-buffered saline wash buffer (20 $\mu$M Tris-HCl, pH 8.0, 50 mM NaCl, 0.2% NP40, 1 mM TLCK, 0.1 mM sodium orthovanadate, 5 mM sodium pyrophosphate) and analyzed by SDS-PAGE using 9% polyacrylamide gels.

In vitro phosphorylation of purified ICP4 proteins with PKA or without added kinase. Approximately 20 ng of the ICP4 protein purified as described previously (Imbalzano, A. N., Shepard, A. A. and DeLuca, N. A., *J. Virol.*, 64:2620–2631 (1990)) was added to a solution containing 10 mM Tris (pH 7.2), 10 mM $MgCl_2$, 50 mM NaCl, 10 mM DTT and 20 $\mu$M (0.15 mCi) [$\gamma$-$^{32}$P]ATP. The phosphorylation reaction was initiated by adding 60 U of protein kinase A type I catalytic subunit purified from bovine heart (Sigma Chem. Co., 1000 U/0.016 mg protein). Reaction mixtures were incubated at 30° C. for 30 min and stopped by addition of SDS-sample buffer. Equal portions of the reactions were analyzed by SDS-PAGE and transferred onto a nitrocellulose sheet for exposure to Kodak X-AR film and for staining with an ICP4-specific antibody. In some cases, the reaction mixtures were terminated by addition of 0.5 ml lysis buffer, and immunoprecipitation was conducted exactly as described above.

In vitro phosphorylation of purified ICP4 proteins with PKC. Approximately 20 ng of purified ICP4 protein was added to a solution containing 20 mM Hepes (pH 7.4), 10 mM $MgCl_2$, 1 mM $CaCl_2$, 100 mg/ml phosphatidylserine, 6 $\mu$g/ml diolein, and 20 mM (0.15 mCi) [$\gamma$-$^{32}$P]ATP. Reactions were initiated by addition of 50–100 U protein kinase C purified from rat brain (Promega).

Two-dimensional phosphopeptide analysis.

(i) Preparation of tryptic peptides. Regions of unfixed polyacrylamide gels containing $^{32}$P-labeled ICP4 proteins were excised using the autoradiogram as a template. The gel slices were then crushed and boiled for 5 min in 1 ml of 50 mM ammonium bicarbonate, pH 7.3, containing 0.1% SDS and 5% 2-mercaptoethanol followed by shaking overnight at room temperature. The eluted proteins were then precipitated on ice for 2 h by addition of 200 $\mu$l of 100% trichloroacetic acid in the presence of 20 $\mu$g of RNase A as carrier. The pellet was washed with 100% ethanol (−20° C.), resuspended in 50 $\mu$l of performic acid (8 parts 99% formic acid, 1 part 30% hydrogen peroxide, 1 part deionized $H_2O$) and incubated for 1 h on ice. The oxidized protein was then lyophilized and washed twice with water before digestion with 20 $\mu$g of TPCK-treated trypsin (Worthington Biochemical Corp.) in 50 $\mu$l of 50 mM ammonium bicarbonate, pH 8.0. The digested protein was again lyophilized and washed with distilled water four times. Approximately equal amounts of protein based on Western blots (corresponding to approximately 1000 Cerenkov cpm of the wt protein) were resolved in two dimensions on 20×20 cm 100 μm thin-layer cellulose (TLC) plates (EM Science).

(ii) Separation of tryptic peptides. Peptides were dissolved in 10 μl of pH 1.9 solution (88% formic acid/acetic acid/water, 25:78:897 (by vol.)] and spotted on TLC plates along with 0.5 μl of tracking dye (a mixture of 5 mg/ml ε-DNP-lysine and 1 mg/ml xylene cyanol blue FF). Electrophoresis was performed towards the cathode in pH 1.9 solution for 28 min at 1000 V followed by ascending chromatography in 1-butanol/acetic acid/pyridine/water, 75:15:50:60 by vol.). The positions of labeled peptides were determined by autoradiography.

Determination of phosphoamino acids. ICP4 proteins or tryptic peptides recovered from TLC plates were hydrolyzed in 50–100 μl of 6N HCl at 110° C. for 70 min. The hydrolysate was then lyophilized and resuspended in 7 μl pH 1.9 solution containing 1 mg/ml cold phosphoamino acid markers (phosphoserine, phosphothreonine, and phosphotyrosine). Routinely, four samples of 30–100 Cerenkov cpm each were spotted on a TLC plate, and electrophoresis was performed for 20 min at 1500 V in a pH 1.9 solution for the first dimension and for 16 min at 1300 V in a pH 3.5 solution (acetic acid/pyridine/water, 10:1:189) for the second dimension. The positions of nonradioactive marker phosphoamino acids were detected by staining with 0.25% ninhydrin.

Peptide sequencing. The phosphopeptides of interest were recovered from TLC plates and eluted from the cellulose with pH 1.9 buffer, followed by one wash with deionized water as described elsewhere (Boyle, W. J., Van Der Geer, P. and Hunter, T., *Methods in Enzymology.*, 201(B):110–148, edited by T. Hunter and B. M. Sefton, (1991)). The peptides were then repeatedly washed and lyophilized to remove any contaminants. N-terminal amino acid sequencing of phosphopeptides was performed at the Core Facility of Dana-Farber Cancer Institute (Boston, Mass.) according to procedures reported previously (Ridley, R. G., Patel, H. V., Gerber, G. E., Morton, R. C. and Freeman, K. B., *Nucleic Acids Res.*, 14:4025–4035 (1986)) using an Applied Biosystems Gas-Phase Model 470A sequenator.

PHOSPHOPEPTIDE ANALYSIS OF ICP4 FROM INFECTED CELLS.

A previous study had shown that the ICP4 protein is phosphorylated on serine and threonine residues (Faber, S. W. and Wilcox, K. W. *Archives of Virol.*, 91:297–312 (1986)), but no information was available on the sites of phosphorylation on ICP4. Therefore, two-dimensional (2-D) phosphopeptide mapping was used to examine the complexity of ICP4 phosphorylation and to attempt to determine the sites on ICP4 that are phosphorylated.

Vero cells were infected with the wild-type virus or ICP4 mutant viruses, n12, n214, n208, d2 or d8-10 as described in Table 4. The infected cells were then labeled with $^{32}$P-orthophosphate from 2.5 to 6.0 h postinfection (pi). Cell extracts were prepared under conditions that solubilize more than 90% of ICP4 (Shepard, A. A., Imbalzano, A. N. and DeLuca, N. A., *J. Virol.*, 63:3714–3728 (1989)). The cell lysates were immunoprecipitated with either monoclonal antibody 58S (for d8-10, KOS1.1, and d2) or polyclonal antibody N15 (for n208 and n214). The immunoprecipitates were subjected to 9% SDS-PAGE. ICP4 was immunoprecipitated from each extract and resolved by SDS-polyacrylamide gel electrophoresis and autoradiography. The bands corresponding to ICP4 polypeptides (indicated by arrows) were excised from the gel, eluted, digested exhaustively with trypsin, and analyzed by two-dimensional phosphopeptide mapping.

Vero cells were infected with KOS1.1, d8-10, n12, d2, n208, or n214 at an moi of 10. At 2.5 h postinfection, the cells were labeled for 3 h with $32P_i$, and total cell extracts were prepared. ICP4 proteins were immunoprecipitated and run on SDS polyacrylamide gels. The ICP4 proteins were then eluted from gel slices, digested with TPCK-trypsin, concentrated by lyophilization and analyzed on TLC plates. Electrophoresis was carried out for 28 min. at 1000 V in pH 1.9 solution with the origin at the lower left and the cathode to the right. Plates were dried and then chromatographed in an ascending buffer from bottom to top. Plates were autoradiographed with intensifying screens to shorten exposure times.

Fourteen spots were consistently observed in independent experiments, and they were labeled numerically (1–10) or alphabetically (a–d). The 14 phosphopeptides were placed into three groups according to their relative intensity. Spots 1–5 were consistently darker than spots 6–10, whereas spots a-d were always lighter than spots 6–10. The material at the origin was likely from undissolved peptides because in some experiments the sample was completely dissolved and separated, and no additional spots were observed. The difference in intensity of these spots indicated that the stoichiometry and/or the turnover rate of the phosphates at different sites were not equivalent. In addition, some spots appeared to be related to each other. For example, the intensity of spots 6 and 7 varied in a reciprocal manner. Spots 9 and 6 lie on a diagonal sloping towards the anode, whereas spots 6 and 7 lie on an opposite diagonal. These observations suggested that spots 9 and 6 may be phosphoisomers with spot 9 being a less phosphorylated form. Spot 7 possibly represented a partial trypsin digestion product of spot 6. Partial digestion products can be caused by a proline residue immediately C-terminal to an arginine residue, by tandemly arranged arginine or lysine residues, or by the presence of phosphorylated serines or threonines adjacent to the cleavage site (Boyle, W. J., Van Der Geer, P. and Hunter, T., *Methods in Enzymology.*, 201(B):110–148, edited by T. Hunter and B. M. Sefton, (1991); Wettenhall, R. E. H., and Morgan, F. J., *J. Biol. Chem.*, 259:2084–2091 (1984)). Therefore the phosphopeptide pattern of ICP4 is complex.

To identify the phosphorylated amino acid residues in each phosphopeptide, $^{32}$P-labeled ICP4 was purified and subjected to HCl hydrolysis or first subjected to phosphopeptide mapping, and then each individual spot was recovered and subsequently subjected to acid hydrolysis. The wild-type ICP4 protein was labeled in vivo with $^{32}$P-orthophosphate and isolated by immunoprecipitation and SDS-PAGE. The purified ICP4 protein was either directly subjected to HCl hydrolysis or first subjected to phosphopeptide mapping and then individual spots were recovered and subsequently subjected to HCl hydrolysis. The hydrolysates were analyzed by electrophoresis at pH 1.9 in the first dimension and at pH 3.5 in the second dimension.

The phosphoamino acids were resolved by two-dimensional electrophoresis. Phosphorylation of wt ICP4 occurred on both serine and threonine residues but not at tyrosine residues. Phosphoserine was the major phosphoamino acid with a ratio to phosphothreonine being about 10:1. These results were consistent with the observations of Faber and Wilcox (Faber, S. W. and Wilcox, K. W. *Archives of Virol.*, 91:297–312 (1986)), who used a ts mutant form of ICP4 labeled at the non-permissive temperature. They were all phosphorylated on serine and threonine residues, although with relatively different ratios. The other phosphopeptides containing both phosphoserines and phosphothreonines are spots 2, 3, 5, and 10. Spots 1, 4, and 8 contained only phosphoserines, while spot a contained only phosphothreonines. The phosphoamino acid residues in spots b–d were not examined because insufficient radioactivity was recovered. The complex phosphopeptide pattern on serine and threonine residues could be due to heterogeneous phosphorylation of one or a few sites or phosphorylation of numerous sites.

PHOSPHORYLATION OF MUTANT ICP4 MOLECULES.

The phosphorylation of several mutant ICP4 molecules were analyzed in an attempt to provide initial mapping of sequences required for phosphorylation. The results from two-dimensional phosphopeptide analysis of mutant ICP4 molecules are summarized in Table 5.

protein structure and altered activities of these mutant ICP4 molecules remain to be elucidated.

The phosphorylation pattern of n12 ICP4, an ICP4 protein with only the amino terminal 250 residues, was phosphorylated on only two spots, one of which co-migrated with spot 7. This result supports the idea that phosphopeptide in spot 7 is contained within the amino terminal 250 residues of ICP4. It should be noted that n12 ICP4 exhibits multiple electrophoretic forms on SDS gels (DeLuca, N. A., and Schaffer, P. A., J. Virol., 62:732–743 (1988)), so the phosphorylation pattern of n 12 ICP4 may be dependent on which of these was isolated.

In summary, the multiple patterns of phosphorylation exhibited by the mutant ICP4 molecules showed a decreasing number of phosphopeptides as more of the ICP4 protein was deleted. This argues strongly that multiple sites on ICP4 are phosphorylated and that the complex phosphopeptide pattern is not due simply to heterogeneous phosphorylation of one site or region.

TABLE 5

Phosphopeptide Mapping Summary

| Virus | Phosphopeptide | | | | | | | | | | | | | |
|---|---|---|---|---|---|---|---|---|---|---|---|---|---|---|
| | 1 | 2 | 3 | 4 | 5 | 6 | 7 | 8 | 9 | 10 | a | b | c | d |
| wt | + | + | + | + | + | + | + | + | + | + | ± | + | + | + |
| d8–10(Δ142–210) | + | + | + | + | + | − | − | + | − | + | + | + + | + + | + |
| n208(1–776) | + | − | ± | + | + | ± | ± | + | + | + | − | − | + + | ± |
| n214(1–591) | ± | − | + + | ± | + | + | − | − | − | − | − | − | − | + |
| d2(Δ185–309) | ± | + | + | + | + | * | * | + | * | + | + | + | + + | − |
| n12(1–250) | − | − | − | − | − | − | + | − | − | − | − | − | − | − |

+ = Spot present
− = Spot absent
++ = Spot with increased intensity
* = New Spot
± = Weak Spot Several different patterns of phosphorylation emerged in that the mutant proteins were missing different numbers of the identified phosphopeptides. The mutant n208 ICP4 containing residues 1–776 was missing only phosphopeptides 2, a, and b. This result indicated that the majority of the phosphopeptides were contained within the amino terminal 776 residues of ICP4. The d8-10 ICP4, missing residues 142–210, lacked phosphopeptides 6, 7, and 9 while the n214 ICP4 molecule contained only phosphopeptides 1, 3, 4, 6, and d. Missing spots could be due to deletion of phosphorylation sites or due to conformational changes in the protein, making the sites unavailable or less available for phosphorylation. Certain mutant ICP4 molecules, the d2 protein in particular, generated unique phosphotryptic peptides with the simultaneous disappearance of the original spots 6, 7, and 9. The new spots may be due to phosphorylation of the serine-rich region from 175 to 185 juxtaposed to the new sequence brought in by the deletion of the residues. Thus, there may be new phosphopeptides containing the serine-rich region. It should be pointed out that the nonsense mutations in n208 or n214, and the deletion in d2 have been shown to affect the ICP4 activities of transactivation, nuclear localization, and DNA binding, respectively (DeLuca, N. A., and Schaffer, P. A., J. Virol., 62:732–743 (1988)). These results show that the same mutant ICP4 molecules exhibit altered phosphorylation. The relationships between the abnormal phosphorylation, altered

PHOSPHORYLATION OF THE SERINE-RICH REGION OF ICP4.

As described above, phosphotryptic peptide analysis of d8-10 ICP4 showed that spots 6, 7, and 9 were missing.

However, when equal molar amounts d8-10 and wild-type ICP4 were analyzed in parallel, it was observed that all of the remaining phosphopeptide spots were underrepresented in d8-10 ICP4 as compared to wild-type ICP4. For example, at least 3-fold longer exposure times were required for d8-10 peptides to give spots with intensity equal to those of wild-type ICP4. From SDS-PAGE analyses, it has been shown that the deletion of the serine-rich region causes about a 90% reduction in ICP4 phosphorylation (Example 1). Given that only a limited number of phosphopeptides were missing in d8-10, it appeared that the large reduction in phosphorylation was due also to decreased phosphorylation of all of the phosphopeptides in the ICP4 molecule. This raised the possibility that ICP4 is differentially phosphorylated at multiple sites and the fully phosphorylated state of ICP4 depends upon a conformational change introduced by the serine-rich region and/or by phosphorylation of the serine-rich region. Thus, the phosphorylation of the multiple sites in ICP4 could be due to a sequential or step-wise mode with phosphorylation of the serine-rich region being the primary event. Alternatively, some of the missing spots may be caused by a conformational change resulting from the deletion of the serine-rich region, so that these phosphorylation sites become inaccessible to protein kinases.

To confirm that the serine-rich region was indeed phosphorylated, spots 7 and 9 were eluted from TLC plates for N-terminal peptide sequencing. The sequencing data showed that spot 7 had the sequence: N-arg-arg-arg-his-gly-arg-trp-arg (SEQ ID NO: 3), which corresponds to residues 166–173 of the serine-rich region of ICP4 (FIG. 4). However, spot 9, although isolated in the same manner as spot 7, could not be sequenced due either to an N-terminal block or to insufficient recovery, possibly because spot 9 is more hydrophobic and the efficiency of elution from cellulose was rather low. Given that the spots 6, 7 and 9 were all phosphorylated on the serines and threonines with relatively different ratios and by examining the sequence of the serine-rich region it is known that there are nineteen serines and only one threonine between amino acids 166–215. Therefore, the single threonine at residue 180 must be phosphorylated on at least some molecules, and multiple serines were also phosphorylated in the serine-rich region. Deletion of the entire serine-rich region has been shown to reduce the activity of ICP4 in transactivation of early genes (Paterson, T. and Everett, R. D., *J. Gen. Virol.*, 71:1775–1783 (1990); Shepard, A. A., Imbalzano, A. N. and DeLuca, N. A., *J. Virol.*, 63:3714–3728 (1989)) as well as late genes. The data show that this deletion not only removes several phosphorylated peptides but also decreases phosphorylation of other parts of ICP4.

IN VITRO PHOSPHORYLATION OF ICP4.

The sites of phosphorylation in in vitro reactions were also defined because, as shown in Example 1, PKA phosphorylation of purified ICP4 was dependent on the presence of the serine-rich region. ICP4 proteins were purified from KOS or d8-10 infected Vero cells as described (Imbalzano, A. N., Shepard, A. A. and DeLuca, N. A., *J. Virol.*, 64:2620–2631 (1990)). Approximately 0.3 µg of each samples were subjected to 9% SDS-PAGE and stained with Coomassie brilliant blue R250 to examine the purity. Purified wild type or d8-10 ICP4 used in these reactions showed a single band on stained gels. PKA or PKC labeled wt ICP4 in these in vitro reactions, and surprisingly, there was some labelling of ICP4 in the reaction mixes without added kinase. To determine whether phosphorylation of ICP4 by PKA, PKC, or without exogenous kinase actually occurred at the in vivo sites, two-dimensional phosphopeptide mapping on labeled ICP4 molecules immunoprecipitated from the reactions was conducted. The positions of individual phosphopeptides in each case were then determined by mixing equal numbers of counts of the in vitro tryptic peptides with the in vivo labeled peptides and observing whether the spots co-migrated. With ICP4 labeled in vitro with PKA, eight phosphopeptides were apparent, and two of them co-migrated with in vivo spots 6 and 7. Phosphopeptide 6 was the peptide most efficiently labeled by PKA. However, for ICP4 phosphorylated in vitro by PKC, seven phosphopeptides were observed, and three of them co-migrated with in vivo spots 6, 7, and 10. Spots 7 and an adjacent novel spot were the peptides most efficiently phosphorylated by PKC. The in vitro phosphopeptide corresponding to in vivo spot 10 exhibited some variability in terms of intensity from experiment to experiment. This variability may be caused by the instability of phosphate groups on this peptide. Furthermore, some new phosphopeptides, such as 9*, were observed in the in vitro phosphorylated proteins. In contrast, in vitro phosphorylation of ICP4 without added kinase showed only one predominant phosphopeptide, and this phosphopeptide co-localized with the in vivo spot 7. Thus, the phosphorylation of ICP4 with PKA or PKC or without added kinase appeared to phosphorylate ICP4 at some of the in vivo sites. More importantly, these results indicated that phosphopeptide 7 may contain sequences needed for each of the three phosphorylation events. As described above, in vivo phosphopeptide 7 represents a fragment between residues 166–215 from the serine-rich region. Therefore, sequences from the serine-rich region are likely to be a target for in vitro phosphorylation.

PHOSPHOAMINO ACID ANALYSIS OF IN VITRO LABELED ICP4 PEPTIDES.

To further characterize the sites of phosphorylation from the in vitro reaction, the identity of the phosphoamino acids from the in vivo labeled wild-type ICP4 and for the phosphopeptide 7 generated by in vivo or in vitro phosphorylation was determined. Both in vivo and in vitro [$^{32}$P]-labeled ICP4 proteins were purified and either directly subjected to HCl hydrolysis or first subjected to phosphopeptide mapping. Spot 7 was then recovered and subsequently subjected to HCl hydrolysis. The hydrolysates were analyzed by electrophoresis at pH 1.9 in the first dimension and at pH 3.5 in the second dimension. Phosphorylation of the wild-type ICP4 protein occurred at both serine and threonine residues but not at tyrosine residues. Phosphoserine was the major phosphoamino acid with the ratio to phosphothreonine being about 10:1. The in vitro "antophosphorylated" peptide (AUTO) contained only phosphoserine residues, while the in vitro phosphorylated peptide 7 by PKA (PKA) or PKC (PKC) contained both phosphoserines and phosphothreonines. Notably, the ratios of phosphoserines to phosphothreonines were different among PKA, PKC, or in vivo phosphorylated peptide 7 (SPOT 7). In the serine-rich region, there are 19 serines and only one threonine at amino acid residue 180. Therefore, this single threonine must be phosphorylated in addition to multiple serines in the serine-rich region of ICP4 from infected cells. These results also indicated that in the serine-rich region, more than one serine residue and the threonine residue were modified by protein kinase A, whereas at least one serine and one threonine were modified by protein kinase C in the in vitro phosphorylation. Alternatively, the different ratios between phosphoserines and phosphothreonines might reflect different turnover rates of phosphate groups on these two amino acid residues. The data obtained from the phosphopeptide mapping and phosphoamino acid analysis suggested that the phosphorylation of ICP4 by PKA or PKC occur at some sites that are similar to and some that are different from those phosphorylated by the kinase activity associated with ICP4.

PROTEIN KINASE ACTIVITY ASSOCIATED WITH ICP4.

While performing the in vitro phosphorylation experiments, it was observed that incubation of the highly purified, wild-type ICP4 protein with [γ-32P]ATP in the absence of added kinase resulted in the incorporation of low levels of label into ICP4. When an equivalent amount of d8-10 ICP4 protein was incubated, no labeled band was observed (Example 1; FIG. 5A, lane 3). The amount of phosphorylation in the absence of added enzyme was approximately one-tenth the level of phosphorylation in the presence of PKA. This phosphorylation in the absence of added enzyme may have resulted from an enzyme tightly bound to ICP4 or from an activity intrinsic to ICP4 itself. Different reaction conditions were also examined to determine the optimal conditions. It was found that this reaction was dependent upon 10 mM $Mg^{+2}$ but inhibited by the presence of 1 mM $Mn^{+2}$, conditions which appear to be different from many of cellular or viral proteins undergoing autophosphorylation (DeLuca, N. A., McCarthy, A. and Schaffer, P. A. J. Virol., 56:558–570 (1985); Knipe, D. M., Ruyechan, W. T., Roizman, B. and Halliburton, I. A., Proc. Natl. Acad. Sci. USA., 75:3896–3900 (1978); Kristie, T. M., and Roizman, Proc. Natl. Acad. Sci., USA, 83:3218–3222 (1986)). Purified ICP4 protein incubated at a very dilute concentration (about 0.1 ng/25 μl reaction) was found to still be phosphorylated, consistent with a mono-molecular reaction. Therefore, there is an unusual kinase activity associated with ICP4.

ICP4 FROM ICP27 MUTANT-INFECTED CELLS SHOWS ALTERED PHOSPHORYLATION.

Rice and Knipe (Rice, S. A. and Knipe, D. M., J. Virol., 62:3814–3823 (1988)) first showed that the electrophoretic mobility of ICP4 was decreased in cells infected with ICP27 ts mutants at the NPT, and Su and Knipe (Su, L., and Knipe, D. M., Virology, 170:496–504 (1989)) showed that expression of ICP27 with ICP4 in transfected cells increased the mobility of ICP4. McMahan and Schaffer (McMahan, L. and Schaffer, P. A., J. Virol., 64:3471–3485 (1990)) later observed a similar effect in cells infected with ICP27 null mutants. To investigate whether ICP27 indeed leads to an alteration of phosphorylation of ICP4, Vero cells were infected with wild-type or ICP27 null mutant (d27-1) viruses, the cultures were labeled with $^{32}$P-orthophosphate, and the ICP4 was purified. The HSV-1 KOS1.1 d27 mutant virus was propagated on V27 cells (Rice, S. A., Su, L. and Knipe, D. M., J. Virol., 63:3399–3407 (1989)).

Two-dimensional phosphopeptide mapping was conducted for the ICP4 proteins isolated from wt or d27-1 infected Vero cells to more closely examine the effect of ICP27 on the decrease of ICP4 electrophoretic mobility. Vero cells were infected with KOS 1.1 or d27-1 at an moi of 10. The labeling and isolation of ICP4 tryptic peptides and the 2-D mapping were performed exactly as described above. Plates were autoradiographed with intensifying screens to shorten exposure times. Several changes were apparent in ICP4 from d27-1-infected cells as compared to ICP4 from wt virus-infected cells. A new spot (labeled with *) appeared and the intensities of spots a, 2, 3, 4, 8, and 9 were significantly increased. However, the intensities of spots 1, 5, 10 and d were decreased. A larger amount of material remained near the origin with d27-1 ICP4, but the differences in the phosphopeptide patterns were reproduced in other experiments. Therefore, ICP27 leads to a change in the phosphopeptide pattern of ICP4, indicating that a viral factor in addition to host factors can affect ICP4 phosphorylation.

DISCUSSION

Although there is evidence that the state of phosphorylation may affect the properties of the HSV ICP4 regulatory protein (Michael, N., Spector, D., Mavromara-Nazos, P., Kristie, T. M. and Roizman, B., Science, 239:1531–1534 (1988); Papavassiliou, A. G, Wilcox, K. W. and Silversrein, S. J., EMBO J., 10:397–460 (1991); Rice, S. A. and Knipe, D. M., J. Virol., 62:3814–3823 (1988); Samaniego, L., Webb, A. and DeLuca, N., J. Virol., 69:5705–5715 (1995); Su, L., and Knipe, D. M., Virology, 170:496–504 (1989)), there has been little detailed information about the sites of phosphorylation on ICP4. The tryptic phosphopeptide patterns of wild-type and mutant ICP4 proteins were examined as a first step towards an understanding of ICP4 phosphorylation sites and how phosphorylation at these sites affects the functions of ICP4. A complex pattern of phosphopeptides was observed from ICP4 labeled in infected cells, and some of these phosphopeptides appeared to be structurally related.

Phosphopeptide analysis of mutant ICP4 molecules containing various portions of the molecule showed at least 5 different peptide profiles with the general pattern being that smaller ICP4 proteins showed fewer phosphopeptides. This was consistent with the idea that ICP4 has several sites of phosphorylation. The results from two-dimensional phosphopeptide mapping of the wild-type and n208 ICP4 indicate that most of the phosphorylation sites reside in the N-terminal half of the molecule. Furthermore, within this part of the molecule there are several functionally important domains such as the DNA-binding domain, regions important for transactivation and the formation of complexes with TFIID and TBP, and a nuclear localization signal. These domains contain consensus motifs for phosphorylation by cellular protein kinase A, protein kinase C, or casein kinase II. In particular, the serine-rich transactivation domain contains consensus motifs for both protein kinase A and casein kinase II.

Phosphorylation of the Serine-rich Region. The serine-rich region of ICP4, residues 142–210, was identified as one target for phosphorylation on ICP4, both in infected cells and in vitro reactions. The d8-10 ICP4, lacking these residues, did not contain the major phosphopeptides, spots 6, 7, and 9 when labeled in infected cells. N-terminal sequencing of spot 7 showed that it arose from the serine-rich region, directly proving that this region is phosphorylated. Phosphoamino acid analysis showed that multiple serine residues and the one threonine residue in this region were phosphorylated.

Despite the observation that only a few spots were missing in the d8-10 ICP4 phosphopeptide pattern total $^{32}$P incorporation into d8-10 ICP4 was reduced by 90% relative to wt ICP4 as shown in Example 1. In addition, nearly all of the phosphopeptide spots were reduced in intensity in d8-10 ICP4 compared to wild-type ICP4. Thus, while the loss of phosphorylation in d8-10 ICP4 can be partially attributed to the loss of phosphorylation in the serine-rich region, the rest appears to be due to a decrease in phosphorylation of other sites. The serine-rich region of ICP4 seems to stimulate phosphorylation of the rest of the molecule, possibly through its own phosphorylation or by changing the conformation of the rest of the protein. Thus, there may be a sequential phosphorylation of multiple sites on ICP4, which could explain the multiple electrophoretic forms of ICP4 seen on SDS-gels.

In vitro Phosphorylation of Purified ICP4 in the Absence of Added Protein Kinases. It was unexpected to find that highly purified ICP4 proteins could undergo phosphorylation without exogenous kinases. This activity could be either an intrinsic property of ICP4 or a tightly associated cellular or viral protein kinase(s). In either case, the same activity plays a role in phosphorylation of ICP4 in vivo because the same phosphopeptide was labeled in vivo. Further insight into this property could be gained by studies on ICP4 proteins purified from an in vitro translation system or from an E. coli or a baculovirus-based expression system. Both cellular proteins, in particular, cell surface receptors (Hunter, T. and Cooper, J. A., Annu. Rev. Biochem., 54:897–930 (1985); Schlessinger, (J., J. Cell Bio., 103:2067–2072 (1986); Yarden, Y. and Ullrich, A., Annu. Rev. Biochem., 57:443–478 (1988)) and viral proteins, for instance, the src protein of Rous sarcoma virus (Collett, M. S., and Erikson, R. L., Proc. Natl. Acad. Sci. USA., 75:2021–2024 (1978)), undergo autophosphorylation. Structural analysis revealed that these proteins usually contain a specific ATP-binding motif (Gly-X-Gly-X-X-Gly) (SEQ ID NO: 4) in their catalytic domains (Hanks, S. K. and Quinn, A. M., Methods in Enzymology, edited by T. Hunter and B. M. Sefton, Part 1, "Protein phosphorylation", 200:38–62 (1991); Leader, D. P., and Katan, M., *J. Gen. Virol.*, 69:1441–1464 (1988)). Examination of the predicted ICP4 amino acid sequence indicates that ICP4 also contains such a motif (Gly-Tyr-Gly-Ala-Ala-Gly) (SEQ ID NO: 6) in residues 515–520. If ICP4 does undergo autophosphorylation, the data supports the conclusion that this region and its flanking sequences possess catalytic activity. Alternatively, if this phosphorylation is due to an associated protein kinase, dissociation of the complex under appropriate conditions should allow purification and identification of the enzyme using known methods.

Effects of HSV ICP27 on ICP4 Phosphorylation and Function. Studies in infected cells (McMahan, L. and Schaffer, P. A., *J. Virol.*, 64:3471–3485 (1990); Rice, S. A. and Knipe, D. M., *J. Virol.*, 62:3814–3823 (1988)) and transfected cells (Su, L., and Knipe, D. M., *Virology*, 170:496–504 (1989)) have shown that ICP27 leads to an electrophoretic shift in ICP4 and stimulation of late gene expression. The electrophoretic shift was hypothesized to be due to changes in phosphorylation of ICP4. The phosphopeptide analysis presented here indicates that ICP4 phosphorylation is indeed altered in cells infected with an ICP27 mutant virus. ICP27, either directly or indirectly, alters protein kinase levels or phosphatase levels so that phosphorylation of ICP4 is altered. The altered ICP4 may then be a more efficient transactivator of late gene expression (McCarthy, A. M., McMahan, L. and Schaffer, P. A., *J. Virol.*, 63:18–27 (1989); Rice, S. A. and Knipe, D. M., *J. Virol.*, 62:3814–3823 (1988); Rice, S. A., Su, L. and Knipe, D. M., *J. Virol.*, 63:3399–3407 (1989); Sacks, W. R., Greene, C. C., Aschman, D. P. and Schaffer, P. A., *J. Virol.*, 55:796–805 (1985)), likely at the level of transcription. The presence of ICP27 may also affect the phosphorylation of ICP4 such that the ability of ICP4 to bind to DNA and repress transcription is affected. Recently, it has been shown that the DNA-binding and repression activity of a mutant ICP4 protein that cannot activate transcription is altered by the presence of ICP27 (Samaniego, L., Webb, A. and DeLuca, N., *J. Virol.*, 69:5705–5715 (1995)). ICP27 has also been observed to be required for viral inhibition of RNA splicing (Hardy, W. R. and Sandri-Goldin, R. M., *J. Virol.*, 68:7790–7799 (1994)) and inhibition or activation of expression of genes containing specific 3' termini or processing signals (Chapman, C. J., Harris, J. D., Hardwicke, M. A., Sandri-Goldin, R. M., Collins, M. K. L. and Latchman, D. S., *Virology*, 186:573–578 (1992); McLaughlin, J., Phelan, A., Loney, C., Sandri-Goldin, R. M. and Clements, J. B., *J. Virol.*, 66:6939–6945 (1992); Sandri-Goldin, R. M. and Mendoza, G. E., *Genes Dev.*, 6:848–863 (1992)). If ICP27 does lead to a general change in protein phosphorylation in infected cells, this could be responsible for the pleiotropic effects of ICP27.

Phosphorylation of ICP4 in the Infected Cell. Based on the results herein and without being bound to any mechanism, the following events are proposed to occur in the infected cell. During productive infection of a permissive cell, ICP4 is first phosphorylated in the serine-rich region by PKA, PKC, or another kinase. This modification allows or promotes a change in conformation in ICP4 so that it can be phosphorylated at other sites in the molecule, fully activating it to interact with cellular transcription factors or DNA and activate transcription. Alternatively, phosphorylation of the serine-rich region may activate a kinase activity associated with or intrinsic to ICP4 which phosphorylates other sites on the ICP4 molecule in cis or trans. Although the serine-rich region of ICP4 stimulates phosphorylation of ICP4 and viral growth, it is not absolutely essential for phosphorylation of ICP4 or viral growth in permissive cells. Therefore, in these cells there are mechanisms for phosphorylation of ICP4 which are independent of the serine-rich region.

In contrast, as described in Example 1, in trigeminal ganglion cells there is a greater restriction of growth of the serine-rich region mutant d8-10 ($10^3$–$10^4$ fold reduction compared to wild-type) than in corneal epithelium ($10^1$–$10^2$ fold reduction compared to wild-type). Thus, there is increased dependence on the serine-rich region of ICP4 for viral replication in the neuronal cells. This may be due to decreased levels of kinases in neurons that phosphorylate ICP4 in the absence of the serine-rich region. The serine-rich region stimulation of phosphorylation of ICP4 may have evolved as a means to accomplish efficient phosphorylation of ICP4 in the neuronal cell where critical kinase levels are low, or it may have evolved as part of a mechanism for sensing the levels of protein kinase activity in a neuronal cell as part of the decision to undergo a productive infection or establish a latent infection in the neuron. Recent results (Kramer, M. F. and Coen, D. M., *J. Virol.*, 69:1389–1399 (1995)) have shown a low level of ICP4 gene transcripts in latently infected ganglia. ICP4 may be expressed at low levels during latent infection, but poorly phosphorylated. Activation or damage of the neuron could activate kinases so that the ICP4 is phosphorylated, initially in the serine-rich region. This would lead to a stimulation of the ICP4 transactivation ability, possibly leading to reactivation. Given the possibility that ICP4 may be present in latently infected ganglia, it may also affect the latent state through its repression activity. Because the ability of ICP4 to bind DNA and repress transcription may also be a function of phosphorylation or the presence of other IE proteins, these activities may also be subject to the same regulatory mechanisms as activation. In these ways, phosphorylation of ICP4 would serve as part of a signal transduction pathway serving to regulate the latent genome in the sensory neuron.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for determining the herpesvirus modulating activity of a compound in a vertebrate cell comprising the steps of:
   a) combining a phosphorylating enzyme capable of catalyzing the phosphorylation of ICP4, a substrate comprising a polypeptide which is phosphorylated by the enzyme, a phosphate source and the compound to be assessed;
   b) maintaining the combination of a) under conditions appropriate for phosphorylation of the substrate; and
   c) determining phosphorylation of the substrate which occurs in the presence of the compound to be assessed, wherein a decrease in the phosphorylation of the substrate indicates inhibition of the herpesvirus infection and an increase in the phosphorylation of the substrate indicates stimulation of the herpesvirus infection.

2. The method of claim 1 wherein the herpesvirus infection is inhibited.

3. The method of claim 1 wherein the phosphorylating enzyme is selected from the group consisting of protein kinase A, protein kinase C, casein kinase II, and ICP4 or an enzymatically functional portion thereof characterized by kinase activity.

4. The method of claim 3 wherein the phosphorylating enzyme is herpes simplex virus type 1 ICP4 or an enzymatically functional portion thereof characterized by kinase activity.

5. The method of claim 4 wherein the enzymatically functional portion of herpes simplex virus type 1 ICP4 is a peptide comprising residues 175–198 of ICP4.

6. The method of claim 1 wherein the substrate is all or a portion of isolated or recombinant ICP4.

7. The method of claim 6 wherein the substrate is a peptide comprising residues 165–179 of ICP4.

8. The method of claim 1 wherein the phosphate source is ATP.

9. The method of claim 1 wherein phosphorylation of the substrate is determined using a method selected from the group consisting of SDS PAGE analysis, immunoprecipitation and binding of labeled phosphopeptides to phosphocellulose paper.

10. A method of for determining the herpesvirus modulating activity of a compound in a vertebrate cell comprising the steps of:
   a) combining a phosphorylating enzyme which is capable of catalyzing the phosphorylation of ICP4, isolated or recombinant ICP4 or a portion thereof which is phosphorylated by the enzyme, a phosphate source and the compound to be assessed;
   b) maintaining the combination of a) under conditions appropriate for phosphorylation of the ICP4; and
   c) determining the amount of phosphorylation of the substrate which occurs in the presence of the compound to be assessed, wherein a decrease in the phosphorylation of the substrate indicates inhibition of the herpesvirus infection and an increase in the phosphorylation of the substrate indicates stimulation of the herpesvirus infection.

11. The method of claim 10 wherein the herpesvirus infection is inhibited in a vertebrate cell.

12. The method of claim 10 wherein the phosphorylating enzyme is selected from the group consisting of protein kinase A, protein kinase C and casein kinase II, and ICP4 or an enzymatically functional portion thereof characterized by kinase activity.

13. The method of claim 12 wherein the phosphorylating enzyme is herpes simplex virus type 1 ICP4 or an enzymatically functional portion thereof characterized by kinase activity.

14. The method of claim 13 wherein the enzymatically functional portion of herpes simplex virus type 1 ICP4 is a peptide comprising residues 175–198 of ICP4.

15. The method of claim 10 wherein the phosphate source is ATP.

16. The method of claim 10 wherein phosphorylation of the substrate is determined using a method selected from the group consisting of SDS PAGE analysis, immunoprecipitation and binding of labeled phosphopeptides to phosphocellulose paper.

17. A method for determining the herpesvirus modulating activity of a compound in a vertebrate cell comprising the steps of:
   a) combining a substrate comprising a polypeptide which is phosphorylated by ICP4 or a portion thereof characterized by kinase activity which is capable of catalyzing the phosphorylation of the substrate, a phosphate source and the compound to be assessed;
   b) maintaining the combination of a) under conditions appropriate for phosphorylation of the substrate; and
   c) determining the amount of phosphorylation of the substrate which occurs in the presence of the compound to be assessed, wherein a decrease in the phosphorylation of the substrate indicates inhibition of the herpesvirus infection and an increase in the phosphorylation of the substrate indicates stimulation of the herpesvirus infection.

18. The method of claim 17 wherein the herpesvirus infection is inhibited.

19. The method of claim 17 wherein the substrate is all or a portion of isolated or recombinant ICP4.

20. The method of claim 19 wherein the substrate is a peptide comprising residues 175–198 of ICP4.

21. The method of claim 17 wherein the phosphate source is ATP.

22. The method of claim 17 wherein phosphorylation of the substrate is determined using a method selected from the group consisting of SDS PAGE analysis, immunoprecipitation and binding of labeled phosphopeptides to phosphocellulose paper.

23. A method for determining the herpesvirus modulating activity of a compound in a vertebrate cell comprising the steps of:
   a) combining all or a portion of an isolated or recombinant ICP4-associated kinase which is capable of catalyzing the phosphorylation of ICP4, isolated or recombinant ICP4 which is phosphorylated by ICP4 or a portion thereof characterized by kinase activity, a phosphate source and the compound to be assessed;
   b) maintaining the combination of a) under conditions appropriate for phosphorylation of the ICP4; and
   c) determining the amount of phosphorylation of the ICP4 which occurs in the presence of the compound to be assessed, wherein a decrease in the phosphorylation of the substrate indicates inhibition of the herpesvirus infection and an increase in the phosphorylation of the substrate indicates stimulation of the herpesvirus infection.

24. The method of claim 23 wherein the herpesvirus infection is inhibited.

25. The method of claim 23 wherein the phosphate source is ATP.

26. The method of claim 23 wherein phosphorylation of the substrate is determined using a method selected from the group consisting of SDS PAGE analysis, immunoprecipitation and binding of labeled phosphopeptides to phosphocellulose paper.

* * * * *

UNITED STATES PATENT AND TRADEMARK OFFICE
CERTIFICATE OF CORRECTION

| | | |
|---|---|---|
| PATENT NO. | : 5,869,234 | Page 1 of 1 |
| APPLICATION NO. | : 08/583569 | |
| DATED | : February 9, 1999 | |
| INVENTOR(S) | : Knipe et al. | |

It is certified that error appears in the above-identified patent and that said Letters Patent is hereby corrected as shown below:

In the Specification

At Column 1, Line number 5, please delete the paragraph labeled "FUNDING STATEMENT" and replace it with the following paragraph:
GOVERNMENT SUPPORT
This invention was made with government support under AI020530 awarded by the National Institutes of Health. The government has certain rights in the invention.

Signed and Sealed this
Seventeenth Day of December, 2024

Derrick Brent
*Acting Director of the United States Patent and Trademark Office*

SEQUENCE LISTING ( 1 ) GENERAL INFORMATION:

( i i i ) NUMBER OF SEQUENCES: 6

( 2 ) INFORMATION FOR SEQ ID NO:1:

(i) SEQUENCE CHARACTERISTICS:
  (A) LENGTH: 69 amino acids
  (B) TYPE: amino acid
  (C) STRANDEDNESS:
  (D) TOPOLOGY: linear (xi) SEQUENCE DESCRIPTION: SEQ ID NO:1:

```
Ala Pro Leu Arg Gly Ala Tyr Pro Asp Pro Thr Asp Arg Leu Ser Pro
1               5                   10                  15
Arg Pro Pro Ala Gln Pro Pro Arg Arg Arg His Gly Arg Trp Arg
                20              25                  30
Pro Ser Ala Ser Ser Thr Ser Ser Asp Ser Gly Ser Ser Ser Ser Ser
            35              40                  45
Ser Ala Ser Ser Ser Ser Ser Ser Ser Asp Glu Asp Glu Asp Asp Asp
        50              55                  60
Gly Asn Asp Ala Ala
65
```

(2) INFORMATION FOR SEQ ID NO:2:

(i) SEQUENCE CHARACTERISTICS:
    (A) LENGTH: 15 amino acids
    (B) TYPE: amino acid
    (C) STRANDEDNESS:
    (D) TOPOLOGY: linear (xi) SEQUENCE DESCRIPTION: SEQ ID NO:2:

```
Arg Arg Arg Arg His Gly Arg Trp Arg Pro Ser Ala Ser Ser Thr
1               5                   10                  15
```

(2) INFORMATION FOR SEQ ID NO:3:

(i) SEQUENCE CHARACTERISTICS:
    (A) LENGTH: 8 amino acids
    (B) TYPE: amino acid
    (C) STRANDEDNESS:
    (D) TOPOLOGY: linear (xi) SEQUENCE DESCRIPTION: SEQ ID NO:3:

```
Arg Arg Arg His Gly Arg Trp Arg
1               5
```

(2) INFORMATION FOR SEQ ID NO:4:

(i) SEQUENCE CHARACTERISTICS:
    (A) LENGTH: 6 amino acids
    (B) TYPE: amino acid
    (C) STRANDEDNESS:
    (D) TOPOLOGY: linear (xi) SEQUENCE DESCRIPTION: SEQ ID NO:4:

```
Gly Xaa Gly Xaa Xaa Gly
1               5
```

(2) INFORMATION FOR SEQ ID NO:5:

(i) SEQUENCE CHARACTERISTICS:
    (A) LENGTH: 7 amino acids
    (B) TYPE: amino acid
    (C) STRANDEDNESS:
    (D) TOPOLOGY: linear (xi) SEQUENCE DESCRIPTION: SEQ ID NO:5:

```
Leu Arg Arg Ala Ser Leu Gly
1               5
```

( 2 ) INFORMATION FOR SEQ ID NO:6:

( i ) SEQUENCE CHARACTERISTICS:
      ( A ) LENGTH: 6 amino acids
      ( B ) TYPE: amino acid
      ( C ) STRANDEDNESS:
      ( D ) TOPOLOGY: linear ( x i ) SEQUENCE DESCRIPTION: SEQ ID NO:6:

Gly  Tyr  Gly  Ala  Ala  Gly
   1                  5